(12) United States Patent
Zhang et al.

(10) Patent No.: US 8,133,474 B2
(45) Date of Patent: Mar. 13, 2012

(54) SENSORS FOR FLUORESCENCE AND MAGNETIC RESONANCE IMAGING

(75) Inventors: Xiao-An Zhang, Somerville, MA (US); Alan Pradip Jasanoff, Cambridge, MA (US); Stephen J. Lippard, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1064 days.

(21) Appl. No.: 11/901,245

(22) Filed: Sep. 14, 2007

(65) Prior Publication Data

US 2008/0138292 A1 Jun. 12, 2008

Related U.S. Application Data

(60) Provisional application No. 60/844,956, filed on Sep. 15, 2006.

(51) Int. Cl.
*A61B 5/00* (2006.01)
*C07B 47/00* (2006.01)
*C07D 487/22* (2006.01)

(52) U.S. Cl. ........... 424/9.362; 424/9.6; 540/145

(58) Field of Classification Search .......... 540/145; 424/9.6, 9.362
See application file for complete search history.

(56) References Cited

U.S. PATENT DOCUMENTS

| | | |
|---|---|---|
| 4,935,498 A | 6/1990 | Sessler et al. |
| 5,041,078 A | 8/1991 | Matthews et al. |
| 5,120,411 A | 6/1992 | Sessler et al. |
| 5,159,065 A | 10/1992 | Sessler et al. |
| 5,162,509 A | 11/1992 | Sessler et al. |
| 5,252,720 A | 10/1993 | Sessler et al. |
| 5,256,399 A | 10/1993 | Sessler et al. |
| 5,262,532 A | 11/1993 | Tweedle et al. |
| 5,272,142 A | 12/1993 | Sessler et al. |
| 5,292,414 A | 3/1994 | Sessler et al. |
| 5,369,101 A | 11/1994 | Sessler et al. |
| 5,410,045 A | 4/1995 | Sessler et al. |
| 5,432,171 A | 7/1995 | Sessler et al. |
| 5,439,570 A | 8/1995 | Sessler et al. |
| 5,451,576 A | 9/1995 | Sessler et al. |
| 5,457,183 A | 10/1995 | Sessler et al. |
| 5,475,104 A | 12/1995 | Sessler et al. |
| 5,504,205 A | 4/1996 | Sessler et al. |
| 5,525,325 A | 6/1996 | Sessler et al. |
| 5,559,207 A | 9/1996 | Sessler et al. |
| 5,565,552 A | 10/1996 | Magda et al. |
| 5,567,687 A | 10/1996 | Magda et al. |
| 5,569,759 A | 10/1996 | Sessler et al. |
| 5,580,543 A | 12/1996 | Sessler et al. |
| 5,583,220 A | 12/1996 | Sessler et al. |
| 5,587,371 A | 12/1996 | Sessler et al. |
| 5,587,463 A | 12/1996 | Sessler et al. |
| 5,591,422 A | 1/1997 | Hemmi et al. |
| 5,595,726 A | 1/1997 | Magda et al. |
| 5,599,923 A | 2/1997 | Sessler et al. |
| 5,599,928 A | 2/1997 | Hemmi et al. |
| 5,601,802 A | 2/1997 | Hemmi et al. |
| 5,607,924 A | 3/1997 | Magda et al. |
| 5,622,946 A | 4/1997 | Sessler et al. |
| 5,632,970 A | 5/1997 | Sessler et al. |
| 5,633,354 A | 5/1997 | Magda et al. |
| 5,707,605 A | 1/1998 | Meade et al. |
| 5,714,328 A | 2/1998 | Magda et al. |
| 5,733,903 A | 3/1998 | Sessler et al. |
| 5,756,726 A | 5/1998 | Hemmi et al. |
| 5,763,172 A | 6/1998 | Magda et al. |
| 5,798,491 A | 8/1998 | Magda et al. |
| 5,801,229 A | 9/1998 | Sessler et al. |
| 5,837,866 A | 11/1998 | Magda et al. |
| 5,888,997 A | 3/1999 | Sessler et al. |
| 5,955,586 A | 9/1999 | Sessler et al. |
| 5,969,111 A | 10/1999 | Sessler et al. |
| 5,994,535 A | 11/1999 | Sessler et al. |
| 6,004,953 A | 12/1999 | Volpin et al. |
| 6,069,140 A | 5/2000 | Sessler et al. |
| 6,072,038 A | 6/2000 | Sessler et al. |
| 6,207,660 B1 | 3/2001 | Sessler et al. |
| 6,262,257 B1 | 7/2001 | Gale et al. |
| 6,375,930 B2 | 4/2002 | Young et al. |
| 6,482,949 B1 | 11/2002 | Sessler et al. |
| 6,657,058 B1 | 12/2003 | Magda et al. |
| 6,984,734 B2 | 1/2006 | Sessler et al. |
| 2003/0009029 A1 | 1/2003 | Buchholz et al. |
| 2003/0031676 A1 | 2/2003 | Sessler et al. |
| 2004/0023891 A1 | 2/2004 | Mody et al. |

FOREIGN PATENT DOCUMENTS

| | | |
|---|---|---|
| WO | WO 9314093 A1 | 7/1993 |
| WO | WO 9621665 A1 | 7/1996 |
| WO | WO 0132210 A2 | 5/2001 |
| WO | WO 2004089300 A2 | 10/2004 |

OTHER PUBLICATIONS

Aime, S. et al., "A p(O₂)-Responsive MRI Contrast Agent Based on the Redox Switch of Manganese (II/III)—Porphyrin Complexes," *Angew. Chem. Int. Ed.* 2000, 39 (4), 747-750.

*Primary Examiner* — Paul V. Ward

(74) *Attorney, Agent, or Firm* — Wolf, Greenfield & Sacks, P.C.

(57) ABSTRACT

The present invention generally relates to agents and compositions having MRI and/or optical signals, and methods for their use in the determination of an analyte. In some cases, an optical, MRI, or other signal produced by the agent or composition may be affected by the presence of an analyte. Some embodiments of the present invention may provide agents or compositions which are cell permeable. Examples of analytes that may be determined by the present invention include zinc ions, calcium ions, and other biological analytes.

22 Claims, 17 Drawing Sheets

R[8] = CH₂CO₂H or CH₂CO₂CH₃

R[10] = CH₂CO₂H or CH₂CO₂CH₃
R[11] = H or CH₃

SENSORS FOR FLUORESCENCE AND MAGNETIC RESONANCE IMAGING

RELATED APPLICATIONS

This application claims priority under 35 U.S.C. §119(e) to co-pending U.S. Provisional Application Ser. No. 60/844,956, filed Sep. 15, 2006, the contents of which are incorporated herein by reference.

STATEMENT REGARDING FEDERALLY SPONSORED RESEARCH OR DEVELOPMENT

This invention was made with the support under the following government contract: 5-R01-GM065519-06 awarded by the National Institutes of Health. The government has certain rights in the invention.

FIELD OF THE INVENTION

The present invention generally relates to agents and compositions having a magnetic resonance imaging (MRI) signal or an optical signal, and related methods.

BACKGROUND OF THE INVENTION

Sensors for metal ions and other species involved in biological signaling pathways and other biological functions can provide valuable information regarding the physiological roles of the metal ions and/or species and can serve as a tool in the diagnosis of a variety of pathologies. For example, zinc is a ubiquitous and indispensable element in the human body and the second most abundant d-block metal after iron. Disruptions of zinc homeostasis have been implicated in a number of health disorders such as Alzheimer's disease, diabetes, and certain cancers. However, detailed studies of the molecular mechanisms of intracellular $Zn^{2+}$ accumulation, trafficking, and function, or mechanisms for other metal ions or biological species, have been limited due to a lack of suitable methods for detection in living biological systems.

Previous methods have involved the irreversible precipitation of metal complexes, which are typically restricted to use in postmortem samples. Fluorescent metal ion sensors have been investigated, but have been limited due to photobleaching and high background signals caused by light scattering. Additionally, as with other optical methods, fluorescence imaging techniques have limited penetration depth and lateral range, making them unsuitable for global analysis of relatively large and opaque specimens, such as live animals.

By contrast, magnetic resonance imaging (MRI) techniques can noninvasively penetrate deep into an intact, opaque object to provide interior 3D information, although its spatial resolution is relatively low compared with that of fluorescence imaging. As one of the most commonly used clinical diagnostic imaging modalities today, MRI is based on a NMR signal arising predominantly from the protons of water molecules. The sensitivity of MRI can be improved by applying contrast agents, which typically comprise paramagnetic metal ions that can influence the NMR relaxation rates of the proton, enhancing the signal in most cases. Factors that determine the relaxivity of a contrast agent include electron spin properties, water molecule accessibility, time scales for molecular motion, and the like. However, for in vivo applications, many MRI techniques have been limited due to insufficient cell membrane permeability. Moreover, some MRI agents comprise toxic metal ions, which have been shown to dissociate from the MRI agent in physiological conditions due to insufficient stability of the metal complex.

Accordingly, improved compositions and methods are needed.

SUMMARY OF THE INVENTION

The present invention relates to magnetic resonance imaging (MRI) or optical agents comprising a chelator group comprising at least one aromatic heterocycle; a binding moiety covalently attached to the chelator group, wherein the binding moiety is capable of binding an analyte such that an MRI and/or optical property of the agent is shifted upon binding the analyte, wherein the chelator group optionally comprises a metal ion bound to the at least one aromatic heterocycle, and wherein the agent is capable of being inserted into a cell or a portion of a cell.

The present invention also relates to compositions comprising a metal complex comprising a metal ion, at least one aromatic heterocycle chelated to the metal ion, and a binding moiety for an analyte, wherein the metal complex has a determinable magnetic resonance imaging signal upon exposure to magnetic resonance imaging conditions and is capable of being inserted into a cell or a portion of a cell, and wherein the binding moiety is capable of interacting with an analyte to affect the MRI signal of the metal complex.

The present invention also provides methods for determining an analyte comprising providing a MRI or optical agent comprising a chelator group and a binding moiety covalently attached to the chelator group, wherein the agent has an MRI signal or an optical signal and is capable of being inserted into a cell or a portion of a cell; exposing the agent to a sample suspected of containing an analyte, wherein the agent interacts with the analyte, if present, to generate an analyte-bound MRI signal or optical signal that is shifted relative to the MRI signal or optical signal absent the analyte; and determining the shift in the MRI signal or an optical signal of the agent, or lack thereof, thereby determining the presence and/or amount of the analyte in the sample.

Figure 1:
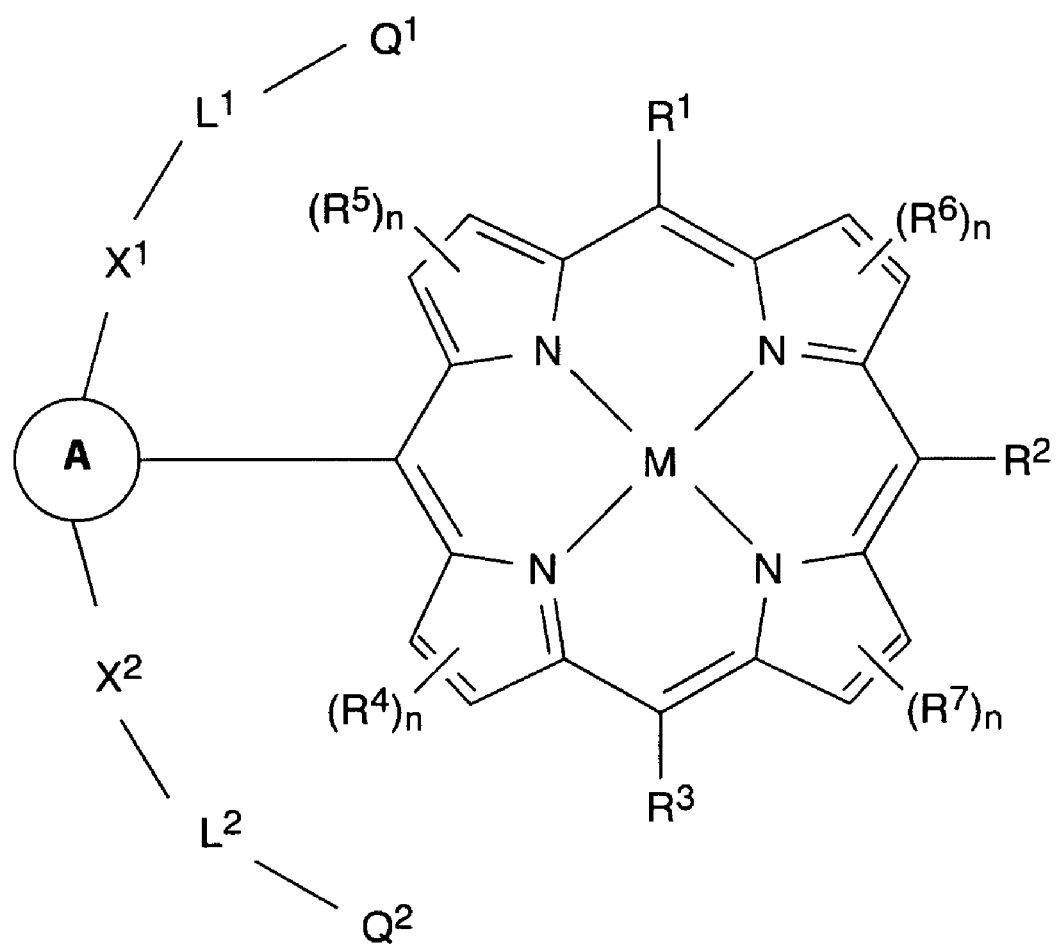
FIG. 1 shows a general formula for a class of porphyrin-based agents, according to some embodiments of the invention.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention generally relates to compounds having MRI and/or optical signals and their use in the analysis of the location, presence, and/or quantity of a particular molecule. In some embodiments, agents or compositions are provided that are detectable in an MRI apparatus, i.e., they are contrast agents that provide information for producing an MRI image, or that are detectable in an optical apparatus, i.e., they are chromophores having a luminescence absorption or emission. In some cases, an optical, MRI, or other signal produced by the agent may be affected by the presence of a particular target analyte.

Some embodiments of the present invention may advantageously provide agents or compositions which are cell permeable, i.e., the agent or composition may be inserted into a cell or portion of a cell, such as the cytoplasm or nucleus. MRI and/or optical agents that are cell permeable may be useful in many applications including in vivo imaging and sensing, either superficially and/or in deep opaque tissue. The use of such agents may facilitate the study of the physiological roles of species including, for example, zinc, calcium, and the like, and may aid in pathological diagnoses. In some cases, embodiments of the invention may exhibit enhanced stability relative to known MRI or optical agents. For example, an agent as described herein may have improved and/or stabilized binding to metal ions in physiological conditions.

Another advantage of the present invention relates to the ability to synthesize a wide variety of agents or compositions having different detection mechanisms (e.g., MRI-based detection, fluorescence-based detection, etc.) and tailored to specifically interact with a particular target analyte, using one or more common synthetic intermediates. For example, the invention may involve the synthesis of a molecular platform that may be easily modified to suit several applications. In some cases, the molecular platform may be bound to a metal ion which may establish the mechanism or property by which the agent determines an analyte. In an illustrative embodiment, the invention may comprise the synthesis of a molecular platform which may be useful as an optical-based (e.g., fluorescence-based) agent. Subsequent binding of the same molecular platform to a paramagnetic metal ion may then produce an MRI-based agent. The molecular platform may also comprise one or more attachment sites for various binding moieties selected to specifically interact with a target analyte.

In some embodiments, the present invention provides methods for determination (e.g., detection) of an analyte, such as zinc ions, calcium ions, nitric oxide, and/or other biological analytes. The agent or composition may comprise a chelator group having an MRI or optical signal and a binding moiety (e.g., for binding an analyte) covalently attached to the chelator group. Determination of the analyte may comprise exposing the agent or composition to a sample suspected of containing an analyte. If present, the analyte can interact with the agent or composition to produce a change in the optical signal or MRI signal of the agent or composition. The shift in the MRI signal or optical signal of the agent may then be determined, thereby determining the analyte. As used herein, the term "determining" generally refers to the analysis of a species or signal, for example, quantitatively or qualitatively, and/or the detection of the presence or absence of the species or signals. "Determining" may also refer to the analysis of an interaction between two or more species or signals, for example, quantitatively or qualitatively, and/or by detecting the presence or absence of the interaction.

For example, the agent may be an MRI-based agent having a first relaxivity upon exposure to magnetic resonance imaging conditions. Exposure of the agent to a sample suspected of containing an analyte, wherein the species interacts with (e.g., binds) the analyte, if present, may then generate a second relaxivity of the analyte-bound species upon exposure to said magnetic resonance imaging conditions. Determination of a change (e.g., shift), or lack thereof, between the first and second relaxivities may then determine the presence and/or amount of the analyte in the biological sample. In some embodiments, the shift in the magnetic resonance imaging signal comprises a shift in T1 relaxivity. In some embodiments, the shift in the magnetic resonance imaging signal comprises a shift in T2 relaxivity.

In another embodiment, the agent may have a luminescence absorption or emission, wherein upon interaction with an analyte, the agent may undergo a change in a characteristic of the luminescence absorption or emission. In some cases, the change comprises a decrease in luminescence intensity of the optical signal. In some cases, the change comprises an increase in luminescence intensity of an optical signal. In some cases, the change comprises a change in the wavelength of the luminescence absorption or emission, either alone or in combination with a change in the luminescence intensity of the optical signal.

In some embodiments, the invention comprises the use of agents (e.g., compounds) that are capable of being inserted into a cell or a portion of a cell, i.e., are cell permeable. As used herein, a species "capable of being inserted into a cell or a portion of a cell" refers to a species which may penetrate the cell membrane and/or interior portions of the cell (e.g., cytoplasm or the nucleus) without substantially damaging the cell or causing cell death. The agent may comprise one or more functional groups that may facilitate interaction between the agent and the cell membrane, transporters positioned within or adjacent the cell membrane, and/or other components associated with the cell that may be involved with cellular uptake of the agent. Such functional groups can include ionic groups, hydrophobic groups, hydrophilic or water-soluble groups, or the like, so long at they, in combination with other features of the species, render the species able to be inserted into a cell, or portion thereof. For example, the agent may comprise one of more sulfonate groups or N-alkyl pyridinium groups.

In one set of embodiments, agents capable of being inserted into a cell or a portion of a cell are those that include one or more functional groups comprising conjugated pi-electron systems (e.g., one or more aromatic groups). Without wishing to be bound by theory, transfer of such an agent across the cell membrane may be facilitated by the delocalization of partial charges in a conjugated pi-electron systems. The aromatic group may be an aryl group, a heteroaryl group (e.g., an aromatic heterocycle), substituted derivatives thereof, and the like. Examples of aromatic groups include phenyl, pyrrole, pyridine, porphyrin, expanded porphyrin groups, or the like, optionally substituted. FIG. 1 shows an illustrative embodiment wherein an agent comprises a porphyrin or metalloporphyrin group.

In some cases, the agent may be capable of being inserted into a cell, or portion thereof, without the need for a carrier molecule, auxiliary membrane-permeating appended group, or other specific conditions or treatments, to enhance cell permeability. In this context, "carrier molecule," or "auxiliary membrane-permeating appended group," or the like means a molecule or group that enhances membrane permeability but is not an integral portion of the agent with respect to its ability to function as an MRI and/or optical agent for determination of an analyte. That is, the "carrier molecule," "auxiliary membrane-permeating appended group," or the like, is not responsible for analyte binding and/or providing properties (e.g., electronic properties) necessary for MRI or optical imaging. For example, the agent may not be linked to carrier molecules such as cell-penetrating peptides, folate, transferrin, the B-subunit of cholera toxin, or other groups which enhance cell permeability of compounds that may otherwise lack or have minimal cell permeability. Some agents described herein may exhibit cell permeability based on the structure and properties of the chelating group and/of binding moiety of the agent, rather than an appended carrier molecule or auxiliary membrane-permeating appended group. In an illustrative embodiment, the agent may be substituted porphyrin group which may be inserted into a cell, or portion thereof.

However, it should be understood that carrier molecules, auxiliary membrane-permeating appended groups, and/or other conditions or treatments may optionally be used in combination with agents and compositions described herein.

Those of ordinary skill in the art would be able to identify whether or not an agent is capable of being inserted into a cell or portion of a cell using simple screening tests. For example, the agent may be incubated with a sample comprising cells, and the cells may be monitored or evaluated using, for example, spectroscopic methods (e.g., absorbance, fluorescence) or the like, to determine the cellular uptake of the agents. In some cases, an agent having a fluorescence emission may be incubated with a sample comprising cells. Observation of the cells using fluorescence microscopy may determine the cellular uptake of the agent within the cells based on the presence of absence of fluorescent material located within the interior of the cell.

As described herein, agents or compositions described herein may comprise a chelator group and a binding moiety covalently attached to the chelator group. The chelator group may be capable of binding a metal ion, such as a paramagnetic metal ion, and the binding moiety may be capable of binding an analyte such that an MRI and/or optical property of the agent is shifted upon binding the analyte. In some embodiments, the agent is an organic or an organometallic compound. As described herein, the presence or absence of a metal ion bound to the chelator group, or, the type of metal ion bound to the chelator group, may affect one or more properties of the agent, such as an MRI or optical property. In some cases, the agent comprises a chelator group which binds a paramagnetic metal ion, such that the agent exhibits an MRI signal upon exposure to MRI conditions, i.e., exposure to a magnetic field. In some cases, the agent comprises a chelator group which does not bind a metal ion or binds a diamagnetic metal ion, such that the agent exhibits a luminescence emission or absorption upon exposure to electromagnetic radiation.

In some cases, the chelator group may comprise one or more heteroatoms which may coordinate or bind a metal atom. Examples of heteroatoms include nitrogen, oxygen, sulfur, etc. In some embodiments, the chelator group comprises at least two, at least three, at least four heteroatoms, or greater. The heteroatom may be located within a cyclic group (e.g., may be a ring atom) or within a linear or branched chain, such as an alkyl chain. In some cases, the chelator group comprises at least one aromatic heterocycle, such pyrrole or pyridine. In some cases, the chelator group may comprise a polycyclic aromatic group. As used herein, the term "polycyclic aromatic" refers to a group comprising at least two aromatic groups. In some cases, the aromatic groups may be fused, i.e., two or more ring atoms are common to two adjoining rings. In some cases, the aromatic groups may be joined via a single bond, or may optionally comprise groups such as alkyl, alkenyl, alkynyl, or aryl groups positioned between the aromatic groups of the polycyclic structure. In some cases, the chelator group comprises a macrocycle, for example, a macrocycle including at least four aryl or heteroaryl rings.

In some embodiments, the chelator group comprises at least one aromatic heterocycle. The chelator group, in some cases, may not be bound to a metal ion. For example, the chelator group may be a free base porphyrin, a free base expanded porphyrin, or a free base polypyrrole group, any of which may be optionally substituted. In some cases, an agent comprising a metal-free chelator group may have a luminescence emission or absorption upon exposure to electromagnetic radiation. In some embodiments, the chelator group comprises at least one aromatic heterocycle and a metal ion bound to the at least one aromatic heterocycle. For example, the chelator group may be a metalloporphyrin, an expanded metalloporphyrin, or a polypyrrole group bound to a metal ion, any of which may be optionally substituted. In some cases, an agent comprises a chelator group bound to a diamagnetic metal ion and the agent may have a luminescence emission or absorption upon exposure to electromagnetic radiation. In some cases, an agent comprises a chelator group bound to a paramagnetic metal ion and the agent may have a relaxivity (e.g., T1 relaxivity, T2 relaxivity) upon exposure to MRI conditions.

Some agents or compositions of the invention may further comprise a binding moiety capable of binding an analyte such that an MRI and/or optical property of the agent is shifted upon binding the analyte. In some embodiments, the binding moiety may be covalently attached to the chelator group. In other embodiments, the binding moiety may be attached to the chelator group via an ionic bond, a hydrogen bond, a dative bond, Van der Waals interactions, or the like. In some cases, the binding moiety may comprise one or more groups capable of interacting with an analyte, or may interact with the analyte combination with one or more portions of the agent. For example, the binding moiety and a heteroatom of a different component of the agent (e.g., a linker portion, or other portion) may together bind an analyte. In some embodiments, the binding moiety may comprise one or more heteroatoms capable of binding a metal ion, nitric oxide, other species present within a cell, or other analyte present with in a subject (e.g., human). In some embodiments, the binding moiety is dipicolylamine (DPA). In some embodiments, the binding moiety is 1,2-bis(o-aminophenoxy)ethane-N,N,N', N'-tetraacetic acid (BAPTA).

In some embodiments, the binding moiety or moieties may interact with a portion of the agent in the absence of an analyte. For example, the agent may comprise a metal ion bound to the chelator group and a binding moiety covalently attached to the chelator group. In the absence of analyte, the binding moiety may bind the metal ion intramolecularly. However, upon exposure to an analyte, the binding moiety may interact with the analyte to a greater extent than the metal ion, such that the analyte-bound binding moiety may dissociate from the metal ion of the chelator group. This may result in a metal ion comprising one or more free coordination sites, wherein other ligands such as water may bind the metal ion. The replacement of the binding moiety as a ligand for the metal ion of the chelator group may affect one or more properties of the agent. For example, the metal ion may be paramagnetic, such that changes in the number and/or type of ligands bound to metal ion may produce a change in an MRI signal of the agent.

Figure 3:
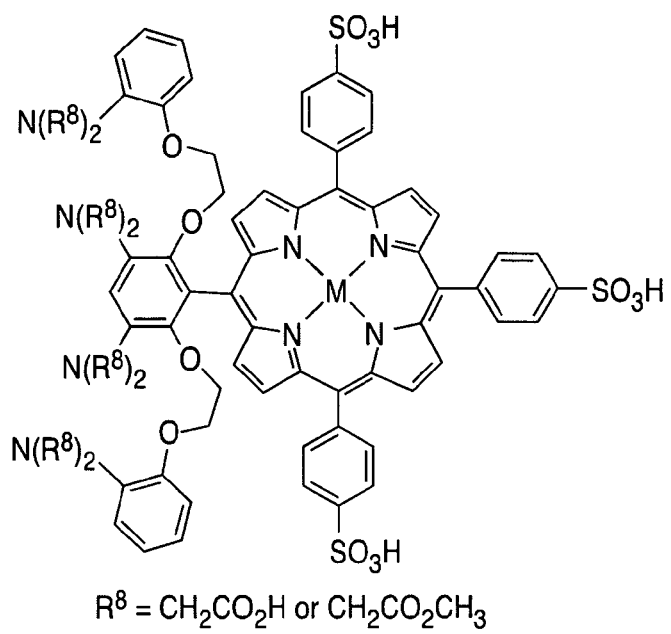
FIG. 3 shows a porphyrin-based calcium sensor, according to one embodiment of the invention.
Figure 3:
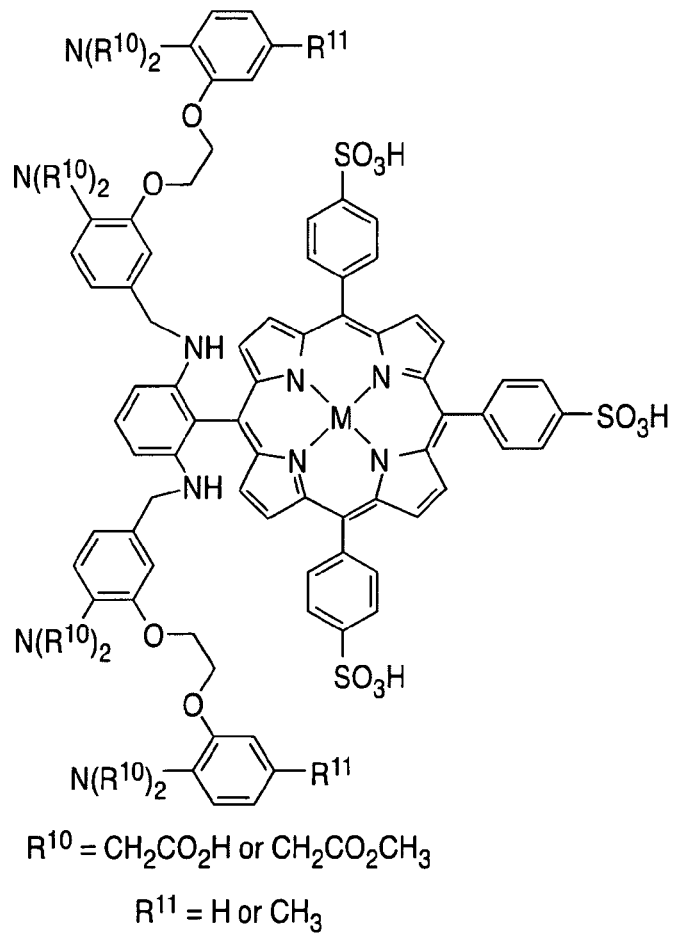

In some embodiments, the binding moiety and/or other portions of the agent may undergo other types of interactions prior to, during, or upon interacting with the analyte, that may enhance the ability of the compound to determine an analyte. For example, the agent may comprise a chelator group and a binding moiety precursor covalently bound to the chelator group, wherein the binding moiety precursor does not interact or interacts to a lesser degree with an analyte, relative to a binding moiety. However, conversion or activation of the binding moiety precursor, i.e., via a chemical reaction such as hydrolysis, may produce a binding moiety capable of interacting with the analyte. In some cases, the binding moiety precursor may be selected to facilitate uptake of the agent within the cell and the binding moiety may be selected to facilitate retention of the compound within the cell. In the illustrative embodiments shown in FIG. 3, a porphyrin molecule may comprise a binding moiety precursor containing ester groups which can enhance the cell permeability of the agent, wherein the ester groups may not interact with, or may minimally interact with, an analyte such as $Ca^{2+}$. Upon uptake within a cell, intracellular enzymes can catalyze hydrolysis of the ester groups to produce BAPTA, a binding moiety capable of specifically binding $Ca^{2+}$. The BAPTA carboxylate groups can also serve to retain or "trap" the compound within the cell.

Some embodiments of the invention relate to compositions comprising a metal complex, wherein the metal complex comprises a metal ion, at least one aromatic heterocycle chelated to the metal ion, and a binding moiety for an analyte, as described herein. The metal complex may have a determinable magnetic resonance imaging signal upon exposure to magnetic resonance imaging conditions and may be capable of being inserted into a cell or a portion of a cell.

Some embodiments of the invention comprise an agent having the formula,

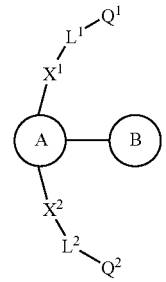

wherein:
A is a group comprising an aryl or heteroaryl group, optionally substituted;
B is a chelator group comprising at least one aromatic heterocycle;
$X^1$ and $X^2$ can be the same or different and each is a heteroatom;
$L^1$ and $L^2$ can be the same or different and each is a group comprising an alkyl or heteroalkyl group, optionally substituted; and
$Q^1$ and $Q^2$ can be the same or different and each is a group comprising a binding moiety for an analyte.

In some embodiments, B comprises a polycyclic group or a macrocycle. For example, B may be a porphyrin, expanded porphyrin, or polypyrrole group, optionally substituted. B may optionally bind a metal ion, such as a paramagnetic metal ion or a diamagnetic metal ion. In some cases, B comprises at least one aromatic heterocycle chelated to a metal ion.

In some embodiments, the agent comprises a porphyrin group and has the formula,

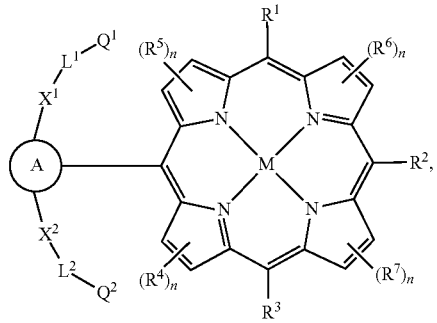

wherein:
A is a group comprising an aryl or heteroaryl group, optionally substituted;
$X^1$ and $X^2$ can be the same or different and each is a heteroatom;

$L^1$ and $L^2$ can be the same or different and each is a group comprising an alkyl or heteroalkyl group, optionally substituted; and $Q^1$ and $Q^2$ can be the same or different and each is a group comprising a binding moiety for an analyte;

$R^{1-3}$ can be the same or different and are groups which are together selected such that the compound is water-soluble;

$R^{4-7}$ can be the same or different and each is hydrogen or a group comprising halide, hydroxyl, alkyl, or aryl, and each is optionally substituted;

M is absent or a metal ion such that, when M is absent, the compound comprises a free base porphyrin group and, when M is present, the compound comprises a metalloporphyrin group.

In some embodiments, A is phenyl or pyridine; both $X^1$ and $X^2$ are N, O, or S; both $Q^1$ and $Q^2$ are dipicolylamine (DPA) or 1,2-bis(o-aminophenoxy)ethane-N,N,N',N'-tetraacetic acid (BAPTA); $R^{1-3}$ are each sulfonated benzene or N-alkylated pyridinium; $R^{4-7}$ are each hydrogen; and M is absent or $Mn^{3+}$, $Mn^{2+}$, $Fe^{3+}$, $Fe^{2+}$, $Zn^{2+}$, $Mg^{2+}$ or $Al^{3+}$.

In one embodiment, the agent has the structure,

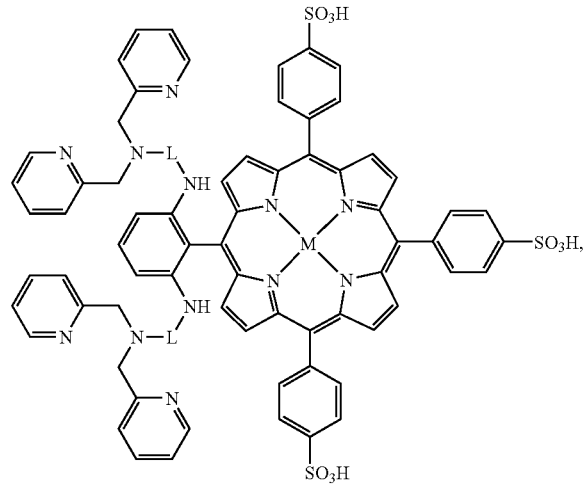

wherein L is an ethylene group and M is $Mn^{3+}$, $Mn^{2+}$, $Fe^{3+}$, or $Fe^{2+}$.

In another embodiment, the agent has the structure,

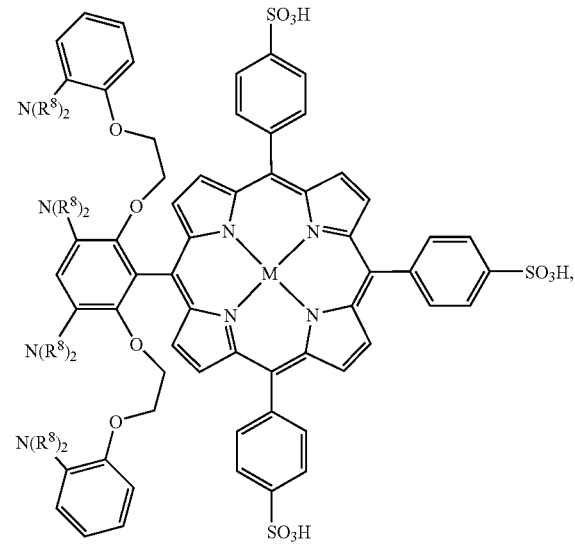

wherein M is $Zn^{2+}$, $Mg^{2+}$, $Al^{3+}$, $Mn^{3+}$, $Mn^{2+}$, $Fe^{3+}$, or $Fe^{2+}$; $R^8$ is $CH_2CO_2H$ or $CH_2CO_2R^9$; and $R^9$ is alkyl.

In another embodiment, the agent has the structure,

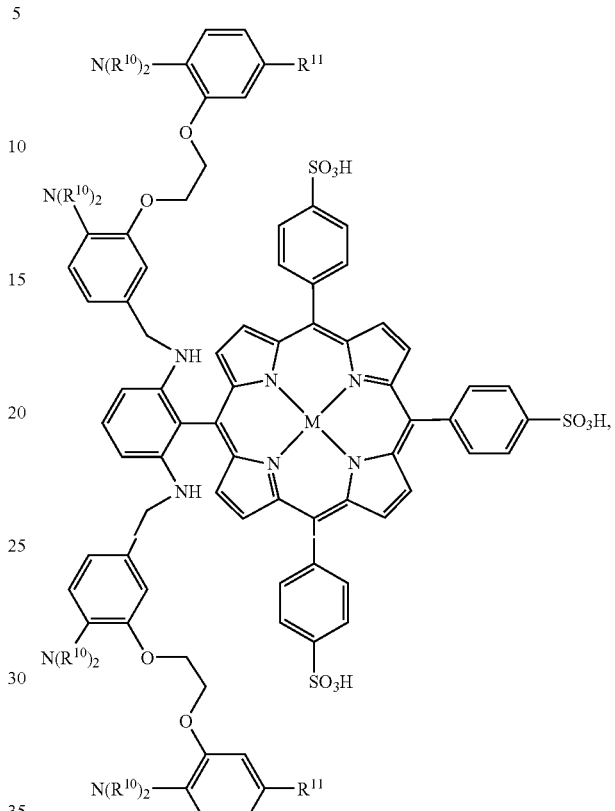

wherein M is $Zn^{2+}$, $Mg^{2+}$, $Al^{3+}$, $Mn^{3+}$, $Mn^{2+}$, $Fe^{3+}$, or $Fe^{2+}$; $R^{10}$ is $CH_2CO_2H$ or $CH_2CO_2R^{12}$; $R^{11}$ is hydrogen or alkyl; and $R^{12}$ is alkyl (e.g., methyl).

In some embodiments, the present invention provides methods for determination of an analyte using any of the agents or compositions as described herein, wherein the agent or composition interacts with the analyte to produce a determinable change in, for example, an MRI or optical property of the agent. In some cases, the interaction between the analyte and the porphyrin compound may comprise binding of the analyte to a portion of the agent or composition. The portion may be the chelator group, a group pendant group to the chelator group (e.g., a binding moiety), a coordination site of a metal ion bound to the chelator group, or a combination of these. For example, the analyte may bind a coordination site of a metal bound to the chelator group as well as one or more pendant groups. In some embodiments, the interaction between the analyte and the agent may comprise formation of a bond, such as a covalent bond (e.g. carbon-carbon, carbon-oxygen, oxygen-silicon, sulfur-sulfur, phosphorus-nitrogen, carbon-nitrogen, metal-oxygen or other covalent bonds), an ionic bond, a hydrogen bond (e.g., between hydroxyl, amine, carboxyl, thiol and/or similar functional groups, for example), a dative bond (e.g. complexation or chelation between metal ions and monodentate or multidentate ligands), or the like. The interaction may also comprise Van der Waals interactions. In one embodiment, the interaction comprises coordination between at least one heteroatom of the binding moiety and an analyte. For example, the agent may comprise a porphyrin as described herein, wherein the analyte may interact with the porphyrin ring, a metal bound to a porphyrin ring, and/or a pendant group of the porphyrin ring.

In some cases, the interaction between the agent and the analyte may comprise a change in the spin state of a metal ion bound to the agent, and/or a change in the accessibility of the metal ion to coordination by ligands such as water. For example, the agent may comprise a paramagnetic metal ion bound to the agent, such that the agent exhibits an MRI signal upon exposure to MRI conditions. Binding of the analyte to the agent can affect the magnitude or type of MRI signal produced by the metal ion. In some cases, the change in the MRI signal comprises a change in the contrast produced by the species in an MRI image.

As used herein, "magnetic resonance imaging conditions" refers to a set of conditions under which a species may generate a magnetic resonance imaging signal. For example, a species comprising a paramagnetic metal ion may be capable of producing an MRI signal having either longitudinal or transverse proton relaxation enhancement, when exposed to MRI conditions. The set of conditions typically comprises exposure to a magnetic field, wherein the resulting MRI signal may be determined by observation of the relaxivity of the species. The MRI signal may also be used to produce an MRI image, wherein the contrast between locations which comprise the species and locations which do not comprise the species may be used to form the image. In some cases, the image may be formed based on the contrast between locations wherein an analyte is present and has interacted with the species, and locations wherein an analyte is not present or is present in a different amount. Those of ordinary skill in the art would understand the use of MRI signals to produce an MRI contrast image.

In some cases, the interaction between the agent and the analyte may comprise, for example, energy transfer (e.g., photoinduced charge transfer, fluorescence resonance energy transfer), electrostatic interactions, binding interactions, redox reactions (e.g., reduction, oxidation), other chemical reactions, and the like. In some embodiments, the interaction between the agent and the analyte may produce a change in an optical signal of the agent, such as a change in luminescence intensity of the optical signal. For example, interaction between an emissive agent and the analyte may produce an increase the luminescence intensity of the agent. The emissive agent may exist in a "quenched" state and may have a small or substantially no emission signal upon exposure to electromagnetic radiation. Upon interaction with an analyte, the analyte may interact with at least a portion of the emissive agent such that an emission signal is generated that has a greater luminescence intensity than the emission signal in the absence of analyte upon exposure to the same conditions of electromagnetic radiation. Alternatively, an emissive agent may, upon exposure to electromagnetic radiation, produce a first emission signal in the absence of an analyte. In the presence of an analyte, the emissive agent may then interact with (e.g., transfer charge to) an analyte and/or another portion of the agent, resulting in a second emission which has decreased or "quenched" luminescence intensity.

In some cases, methods of the invention comprise determining a change in the wavelength of an emission signal. The wavelength of an emission signal refers to the wavelength at which the peak maximum of the emission signal occurs in an emission spectrum. The emission signal may be a particular peak having the largest intensity in an emission spectrum (e.g. a fluorescence spectrum), or, alternatively, the emission signal may be a peak in an emission spectrum that has at least a defined maximum, but has a smaller intensity relative to other peaks in the emission spectrum.

In some embodiments, the change in luminescence intensity of an optical signal produced by the agent may occur for an emission signal with substantially no shift in the wavelength of the luminescence (e.g., emission), wherein the intensity of the emission signal changes but the wavelength remains essentially unchanged. In other embodiments, the change in luminescence intensity of an optical signal produced by the agent may occur for an emission signal in combination with a shift in the wavelength of the luminescence (e.g., emission). For example, an emission signal may simultaneously undergo a shift in wavelength in addition to an increase or decrease in luminescence intensity.

Figure 2:
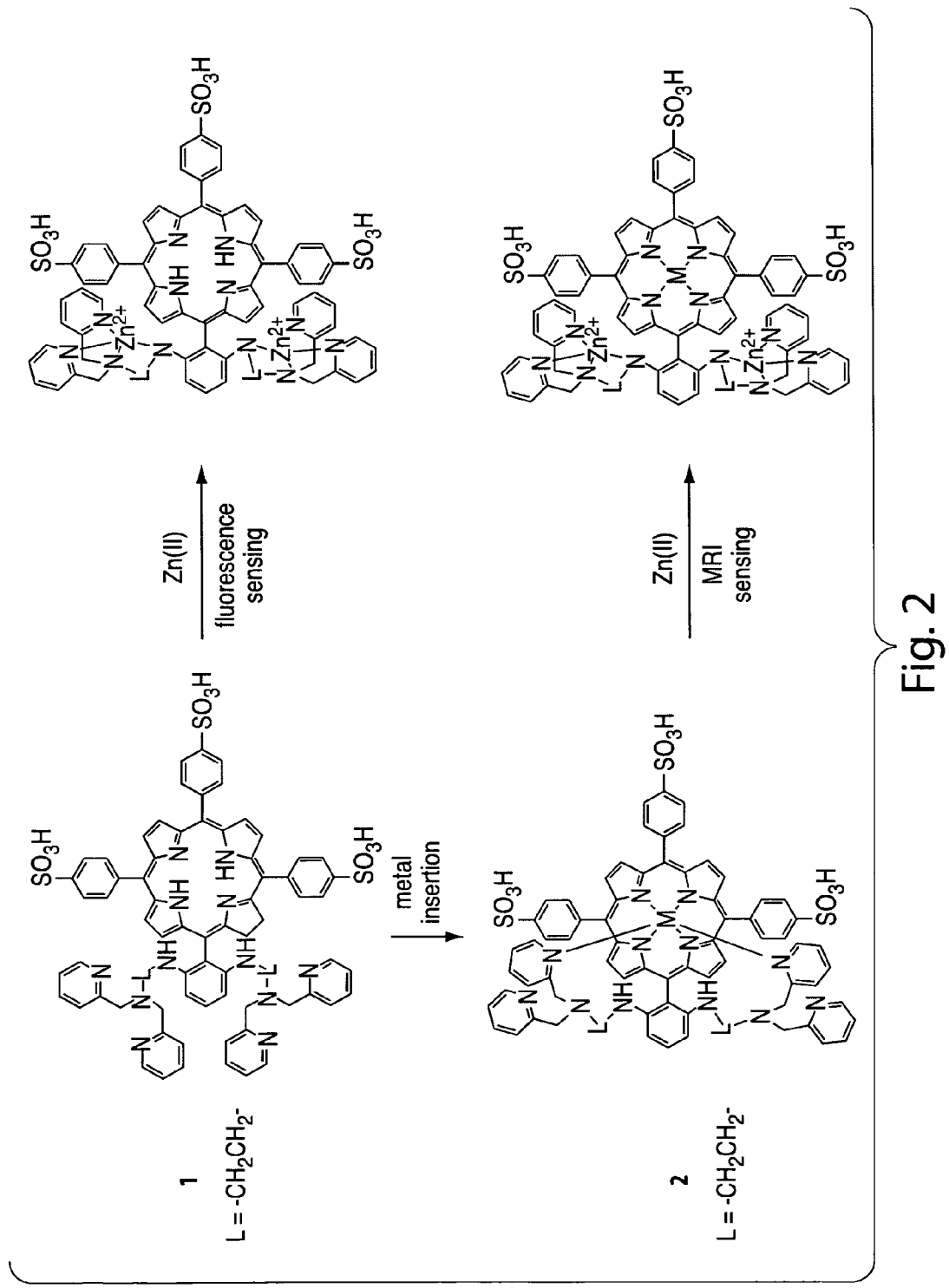
FIG. 2 shows a porphyrin-based sensor that may be useful in both fluorescence and MRI determination of zinc, according to one embodiment of the invention.

FIG. 2 shows an illustrative embodiment of a porphyrin-based agent for determining a zinc analyte. Compound 1 includes two DPA moieties covalently attached to a water-soluble, sulfonated porphyrin ring. In the absence of zinc, the DPA moieties may be positioned in close proximity to top and bottom faces of the porphyrin ring, such that the fluorescence of compound 1, either as a free base porphyrin or as a diamagnetic metallated porphyrin. Without wishing to be bound by theory, the fluorescence emission of compound 1 may be partially quenched by the lone pair electron(s) from the nearby DPA units via, for example, photoinduced electron transfer. Upon exposure to zinc, the DPA groups may bind zinc ions, producing a change in the orbital energy levels of these lone pair electrons and reducing the PET effect, such that the fluorescence intensity of the agent is increased.

By addition of a paramagnetic metal (e.g., $Mn^{3+}$ or $Fe^{3+}$) to compound 1 to form compound 2, an agent having an MRI signal may be generated. (FIG. 2) In the absence of zinc, two pyridine groups of the binding moiety may act as intramolecular, axial ligands to the paramagnetic metal, blocking access of, for example, water molecules to the paramagnetic metal ion. In the presence of zinc, the pyridine groups may bind to the analyte and may withdraw from the paramagnetic metal, generating two free axial metal coordination sites for water and enhancing relaxivity of the complex to generate an analyte-bound MRI signal. This mechanism may allow zinc to be determined by MRI.

Figure 4:
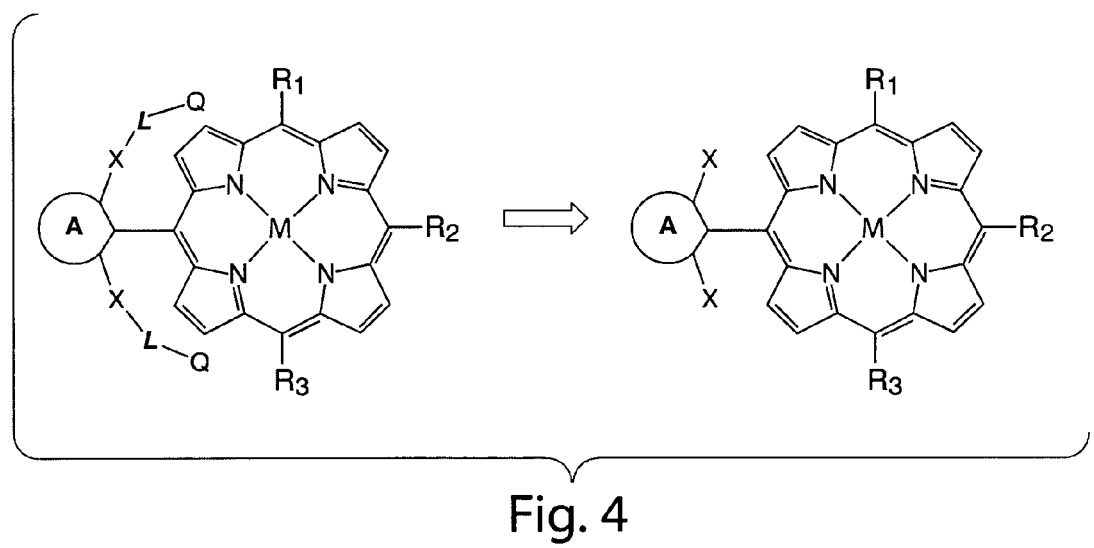
FIG. 4 shows a schematic representation of a retrosynthesis of a sensor, according to one embodiment of the invention.

Agents of the present invention may be synthesized using a variety of known methods. In some cases, synthesis of an agent may comprise attachment of the chelator group to one or more binding moieties, optionally via a linker group(s). The chelator group may comprise at least one functional group capable of forming a bond with a binding moiety, or linker for a binding moiety. For example, the synthesis of agents comprising porphyrin groups may involves acid- or base-catalyzed condensation of pyrroles and aldehyde derivatives, each optionally substituted in accordance with a particular desired product. One or more analyte binding moieties may then be attached to the porphyrin group, as shown by the retrosynthetic scheme in FIG. 4. A binding moiety may be attached to the chelator group via, for example, a condensation reaction between an amine and an aldehyde or a substitution reaction between a nucleophile and an electrophile. In some embodiments, the binding moiety may be attached to the chelator group via a reductive amination reaction. Those of ordinary skill in the art would understand the meaning of these terms. Functional groups that may affect solubility or other properties may be installed before or after the chelator group is attached to the binding moiety. Similarly, a metal ion can optionally be inserted prior to or after the chelator group is attached to the binding moiety.

Figure 16A:
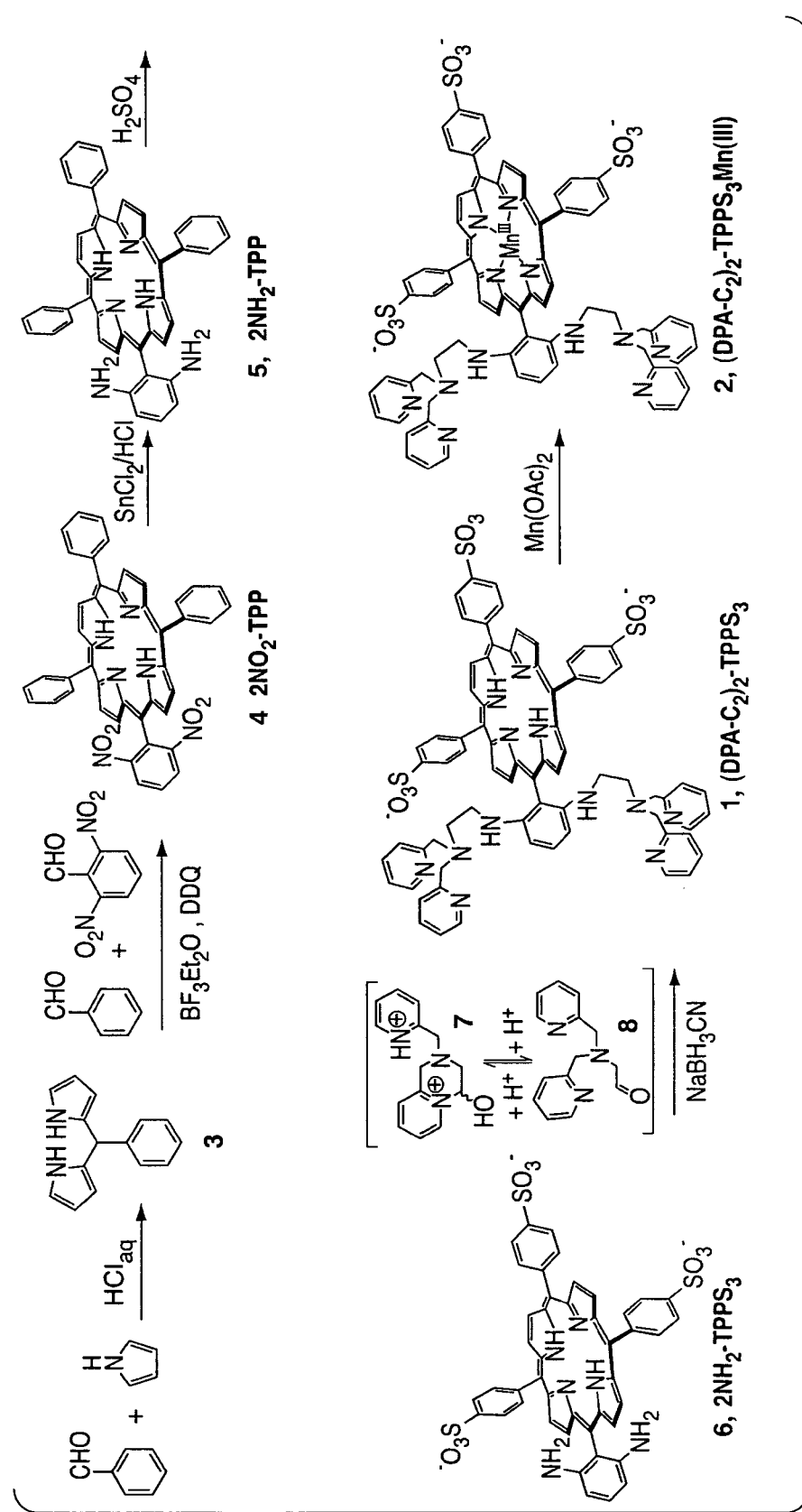
FIG. 16A shows the synthesis of a porphyrin-based zinc sensor, according to one embodiment of the invention.
Figure 16B:
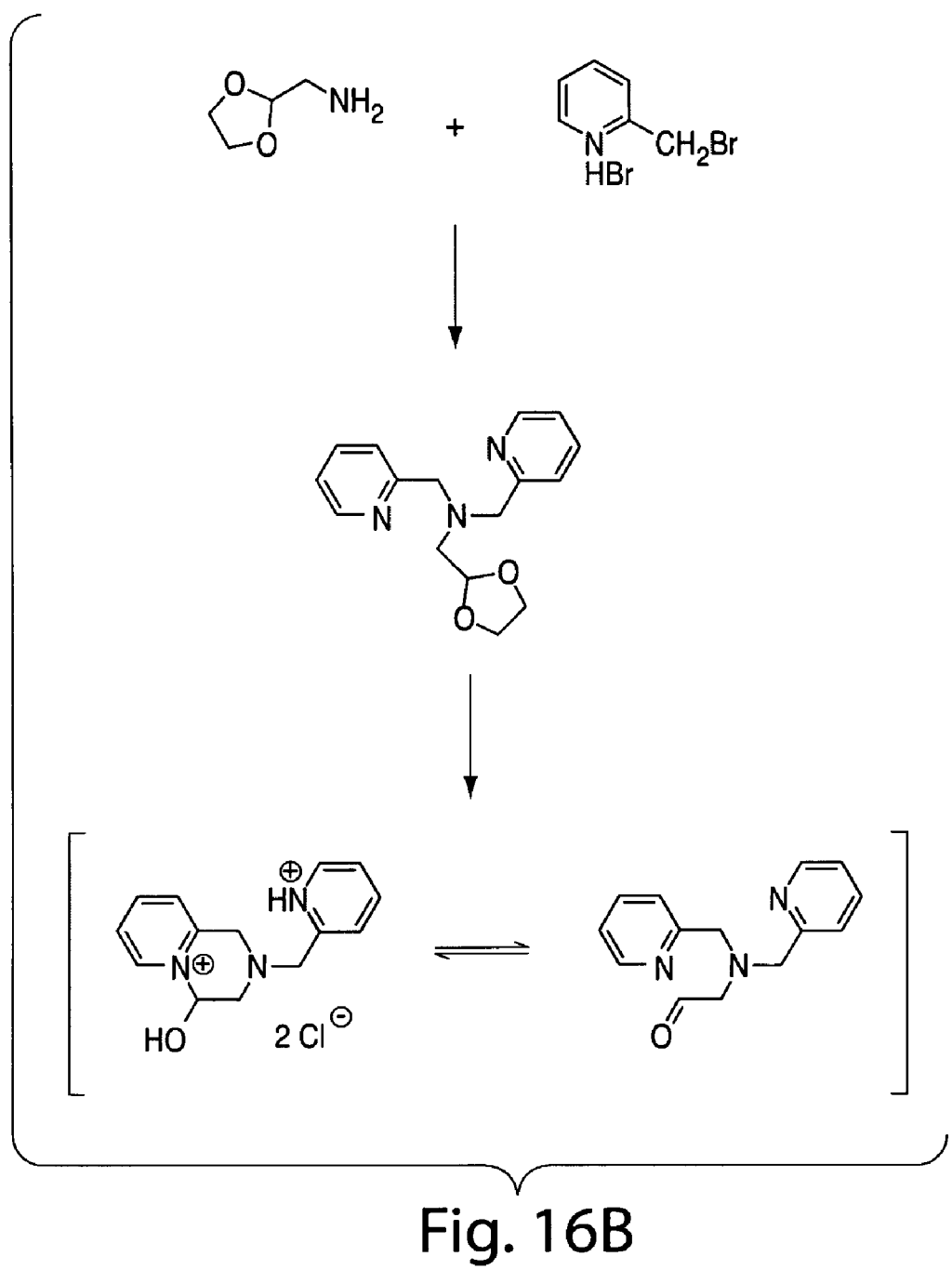
FIG. 16B shows the synthesis of a binding moiety precursor, according to one embodiment of the invention.

As an illustrative embodiment, FIG. 16A shows the synthesis of a porphyrin-based agent for determination of zinc.

The 5-phenyldipyrromethane precursor, compound 3, may be prepared from an aqueous HCl solution and purified by recrystallization from toluene. The condensation of compound 3 with benzaldehyde and 2,6-dinitrobenzaldehyde in the presence of $BF_3.Et_2O$ as a catalyst, followed by in situ oxidation with 2,3-dichloro-5,6-dicyano-1,4-benzoquinone (DDQ), affords the desired dinitrotetraphenylporphyrin ($2NO_2$-TPP, 4). The reduction of $2NO_2$-TPP by stannous chloride in aqueous HCl solution gives $2NH_2$-TPP (compound 5), which may then be allowed to react with concentrated $H_2SO_4$ at 80° C. Under these conditions, highly selective sulfonation only at the para-positions of the three phenyl rings having no attached amino group may be achieved to form a water-soluble product, $2NH_2$-$TPPS_3$ (compound 6), where $TPPS_3$ is 5-phenyl-10,15,20-tris(4-sulfonatophenyl)-porphyrin. The zinc-binding units may then be attached to give compound 1 by reductive amination of compound 6 in the presence of compound 7, which converts to its ring-opened aldehyde form compound 8 upon raising the pH. (FIG. 16A) Manganese(III) ion may be inserted into the porphyrin core by reaction of 1 with manganous acetate in hot N,N-dimethylformamide solution to afford $(DPAC_2)_2$-$TPPS_3Mn(III)$. The reaction may be monitored by UV-visible spectroscopy as a decrease in absorption at 421 nm and an increase at 467 nm. Sufficient removal of $Mn^{2+}$ from the final product may be confirmed by observing the EPR signal, or lack thereof, of the product.

Figure 17:
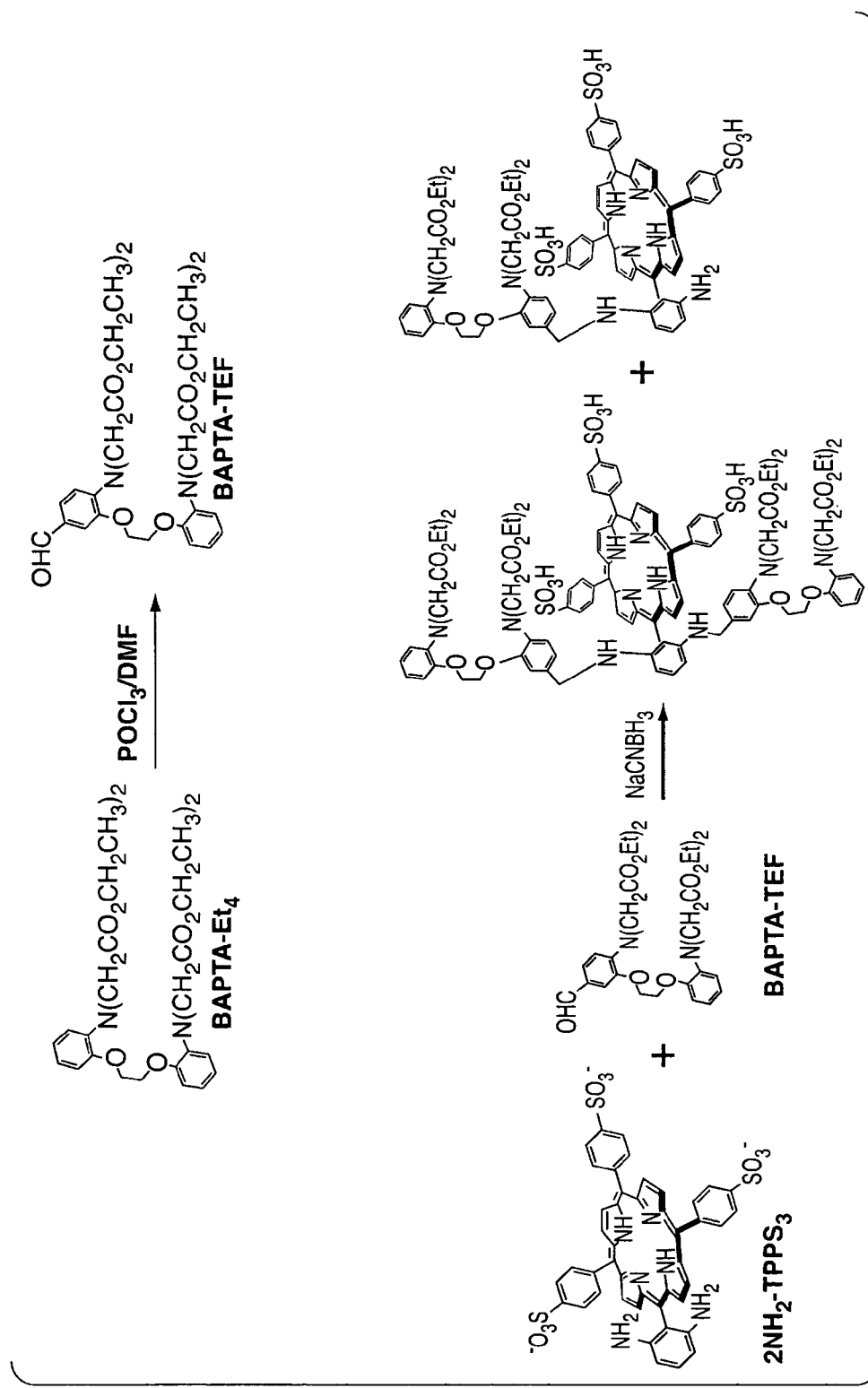
FIG. 17 shows the synthesis of a porphyrin-based calcium sensor, according to one embodiment of the invention.

In another illustrative embodiment, FIG. 17 shows the synthesis of a porphyrin-based agent for determination of calcium ions, wherein a binding moiety precursor comprising an aldehyde (BAPTA-TEF) is prepared and subsequently condensed with a porphyrin ring comprising two amines (e.g., $2NH_2$-$TPPS_3$) to generate a porphyrin-based agent comprising either one or two BAPTA binding moieties for calcium ions.

Synthetic methods described herein can generally be applied to access a wide range of MRI and/or optical sensors for target analytes. In some embodiments, the synthetic methods described herein may eliminate the need for a large excess of pyrrole, for example, in the synthesis of porphyrin-based agents, and/or additional processing steps, including, for example, purification by column chromatography and sublimation steps. In some cases, the synthetic method may be useful in large-scale syntheses of dipyrromethane derivatives, which are common precursors in porphyrin synthesis.

Another aspect of the invention relates to a general synthetic method for functionalizing a species with a DPA group. For example, the method may comprise reacting a species comprising a nucleophile, such as an amine, with a compound having the formula,

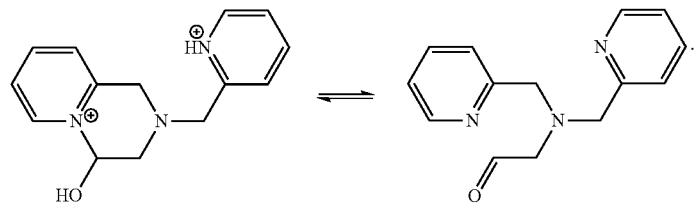

An example of the synthesis of the above compound (e.g., compound 7) is shown in FIG. 16A. Compound 7 may be useful as a general precursor for preparing molecules containing dipicolylamine (DPA) groups and other functional moieties.

Analytes that may be determined using the agents, compositions, and methods described herein include metal ions, nitric oxide, or other species associated with normal biological function. The analyte may be present within a subject (e.g., a human), and, in some cases, may be present within a cell. In some cases, the analyte may be present within a subject in a location exterior to a cell. In some cases, the analyte is a metal ion, such as a toxic metal ion. Examples of metal ions include, but are not limited to, $Zn^{2+}$, $Ca^{2+}$, $Hg^{2+}$, $Cd^{2+}$, $Pb^{2+}$, $Na^+$, $Mg^{2+}$, $Mn^{2+}$, $Fe^{2+}$, $Co^{2+}$, $Ni^{2+}$, and $Cu^{2+}$. In some cases, the analyte is $Zn^{2+}$, $Ca^{2+}$, $Hg^{2+}$, $Cd^{2+}$, or $Pb^{2+}$. In some embodiments, the analyte may be a zinc ion.

In some embodiments, the analyte may be a calcium ion. Calcium is a component of cellular signaling systems and participate in normal brain function. Muscles (including the heart) may also depend on regulation of calcium, and calcium has been implicated in myocardial dysfunction. In one embodiment, an agent or composition of the invention may be useful in the determination of calcium ions within a cell.

The analyte may also include other species associated with normal biological function, including ions, amino acids, peptides, other small molecules, and the like. For example, agents and compositions described herein may be useful in determination of glucose, ATP, cAMP, glutamate, and/or other metabolites and signaling molecules. In one embodiment, an agent or composition of the invention may be useful in the determination of nitric oxide, which is a component of vascular regulatory pathways, mechanisms of inflammation, and neuronal signaling. Those of ordinary skill in the art would be able to select an appropriate binding moiety for a particular analyte, for use in the context of the invention.

The term "paramagnetic metal ion" is known in the art and refers to a metal ion having unpaired electrons, causing the metal ion to have a measurable magnetic moment in the presence of an externally applied field. Examples of suitable paramagnetic metal ions, include, but are not limited to, ions of iron, nickel, manganese, copper, gadolinium, dysprosium, europium, and the like. For example, $Mn^{3+}$, $Mn^{2+}$, $Fe^{3+}$, and $Fe^{2+}$ are examples of paramagnetic metal ions. In some embodiments, an agent or composition of the invention, such as a porphyrin-based agent of the invention, comprises a chelator group bound to a paramagnetic metal ion, wherein the paramagnetic ion is an ion of iron or manganese.

As used herein, an "emission" may be a luminescence emission, in which "luminescence" is defined as an emission of ultraviolet or visible radiation. Specific types of luminescence include fluorescence, phosphorescence, chemiluminescence, electrochemiluminescence, and the like. In some cases, the emission may be fluorescence emission.

In the compounds and compositions of the invention, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl may have 30 or fewer carbon atoms in its backbone, and, in some cases, 20 or fewer. In preferred embodiments, a straight chain or branched chain alkyl has 12 or fewer carbon atoms in its backbone (e.g., $C_1$-$C_{12}$ for straight chain, $C_3$-$C_{12}$ for branched chain), and more preferably 6 or fewer, and even more preferably 4 or fewer. Likewise, preferred cycloalkyls have from 3-10 carbon atoms in their ring structure, and more preferably have 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclohexyl, and the like.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "alkenyl" and "alkynyl" refer to unsaturated aliphatic groups analogous in length and possible substitution to the alkyls described above, but that contain at least one double or triple bond respectively.

The terms "heteroalkenyl" and "heteroalkynyl" refer to unsaturated aliphatic groups analogous in length and possible substitution to the heteroalkyls described above, but that contain at least one double or triple bond respectively.

As used herein, the term "halogen" or "halide" designates —F, —Cl, —Br, or —I.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the The terms "heteroaryl" refers to aryl groups comprising at least one heteroatom as a ring atom.

The term "heterocycle" refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures, more preferably 3- to 7-membered rings, whose ring structures include one to four heteroatoms. The term "heterocycle" may include heteroaryl groups (e.g., aromatic heterocycles), saturated heterocycles (e.g., cycloheteroalkyl) groups, or combinations thereof. The heterocycle may be a saturated molecule, or may comprise one or more double bonds. In some case, the heterocycle is an aromatic heterocycle, such as pyrrole, pyridine, and the like. In some cases, the heterocycle may be attached to, or fused to, additional rings to form a polycylic group. In some cases, the heterocycle may be part of a macrocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "amine" and "amino" are art-recognized and refer to both unsubstituted and substituted amines, e.g., a moiety that can be represented by the general formula: N(R')(R'')(R''') wherein R', R'', and R''' each independently represent a group permitted by the rules of valence. An example of a substituted amine is benzylamine.

Any of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group.

For example, a "substituted phenyl group" must still comprise the phenyl moiety and can not be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

EXAMPLES

Solvents for synthesis were of reagent grade or better. Pyrrole and benzaldehyde were distilled before use. All other reagents were purchased and used as received. Silica gel (230-400 mesh, EMD Chemical) and octadecyl-functionalized silica gel (RP-18, Aldrich) were used for column chromatography. Analytical thin layer chromatography was performed by using Merck60 F254 silica gel or Whatman octadecyl-functionalized plates (precoated sheets, 0.25 mm thick). $^1$H-NMR and $^{13}$C-NMR spectra were collected in CD2C12, CD3OD, or DMSO-d6 (Cambridge Isotope Laboratories, Cambridge, Mass.) at 25° C. at the Massachusetts Institute of Technology Department of Chemistry Instrumentation Facility (DCIF) on a Bruker 400 spectrometer. All chemical shifts were calibrated to residual solvent peaks. ESI-MS spectrometry was performed with an Agilent 1100 Series LC/MSD system. UV-visible spectra were recorded on an HP 8453 spectrometer. IR spectra were obtained on an Avatar 360 FTIR instrument using samples prepared as KBr pellets.

Millipore water was used to prepare all aqueous solutions. All spectroscopic measurements were performed in buffered solutions containing 50 mM of the buffering species and 100 mM KCl adjusted to the desired pH. A glass electrode (Orion, Boston, Mass.), calibrated before each use, was used to determine solution pH. Solutions of $Zn^{2+}$ were prepared from 100 mM stocks of $ZnCl_2$ in water. Absorption spectra were recorded on a 8453A diode array spectrophotometer (Hewlett-Packard, Palo Alto, Calif.) or a Cary 50 Bio UV-visible spectrophotometer (Varian, Palo Alto, Calif.), and fluorescence spectra were obtained with a Quanta Master 4 L-format scanning spectrofluorimeter (Photon Technology International, Lawrenceville, N.J.) equipped with an LPS-220B 75-W xenon lamp and power supply, an A-1010B lamp housing with integrated igniter, a switchable 814 photon-counting/analog photomultiplier detection unit, and a MD-5020 motor driver. Samples for absorption and emission measurements were held in 1×1-cm quartz cuvettes (3.5 mL volume; Stama, Atascadero, Calif.). The experiments for measuring quantum yields, apparent dissociation constants ($K_d$), and metal ion selectivities were performed as described (for example, in Burdette et al., *J. Am. Chem. Soc.* 2001, 123, 7831). Quantum yields were determined by reference to $TPPS_4$ [0.16 in pH=7 aqueous solution].

Suspension-adapted HEK-293 cells (Free-Style 293-F cell line; Invitrogen, Carlsbad, Calif.) were grown in 125-mL shaker flasks containing FreeStyle 293 Expression Medium (Invitrogen). Cultures were maintained at >90% viability on a shaker plate (Titer Plate Shaker; Lab-Line Instruments, Melrose Park, N.J.) moving at 125 rpm in a 37° C. incubator with 8% $CO_2$ and subculturing at a 1:10 ratio upon reaching a density of $2\times10^6$ cells per mL. Cell density and viability were evaluated with a hemocytometer using 0.4% trypan blue staining. Cell pellets for MRI were prepared in 6-mL suspension cultures, to which either compound 2 or $Mn-TPPS_4$ was added to a final concentration of 100 μM and incubated for 24 h. Where appropriate, zinc carried by the ionophore pyrithione (1:1 ratio of zinc/pyrithione) was subsequently added to 200 μM, followed by incubation for an additional 10 min. Cell suspensions were pelleted three times (10 min, 500×g) and washed with PBS, and the resulting loose pellet was inserted into microtiter plates for imaging. Slides of cells growing in adherent monolayers were prepared by plating the suspension-adapted HEK-293 cells in 25-cm2 flasks containing DMEM (Invitrogen) with 10% FBS (HyClone, Logan, Utah). After subculturing five times, cells were grown to 70% confluence on poly-D-lysine-coated glass cover slips and incubated with 5 μM of 1 for 24 h. Cells were then either incubated with 40 μM zinc carried by pyrithione (1:1 ratio) for 10 min, fixed in 4% paraformaldehyde, washed with PBS, and stained with Hoechst 33258 (0.4 μM, 10 min incubation in PBS), or directly fixed, stained with Hoechst dye, and imaged.

The cell fluorescence imaging experiments were performed with an Axiovert 200M inverted epifluorescence microscope (Zeiss, Thomwood, N.Y.) equipped with an EM-CCD digital camera C9100 (Hamamatsu Hamamatsu City, Japan) and a MS200 XY Piezo Z stage (Applied Scientific Instruments, Eugene, Oreg.). An X-Cite 120 metal-halide lamp (EXFO, Quebec, Canada) was used as the light source. The fluorescence images were obtained by using a x63 oil immersion objective lenses and a customized optical filter (exciter: D425/50; emitter: E6001p; beamsplitter: 460dcxr; Chroma Technology, Rockingham, Vt.). The microscope was operated with Volocity software (Improvision, Lexington, Mass.).

Cell monolayers were grown in 75-cm plates to 70% confluence and treated with 100 μM of either 2 or $Mn-TPPS_4$, followed by incubation for 24 h. All fractionation steps were performed at 4° C. After twice pelleting by centrifugation (500×g) and washing with PBS, cells were lysed in a low-salt buffer and incubated on ice for 15 min. After centrifugation (420×g, 5 min) the pellet was resuspended in two packed-cell volumes of lysis buffer with 20 strokes of a 27-gauge syringe needle. After centrifugation (11,000×g, 20 min), the supernatant was retained (cytosolic fraction), and the nuclei were lysed in 0.42 M salt with 10 strokes of a 17-gauge syringe needle. After centrifugation (20,000×g, 5 min), the supernatant was obtained as the nuclear fraction.

Manganese atomic absorption spectroscopic analyses of samples were performed on an Aanalyst 300 instrument equipped with an HGA-800 graphite furnace (PerkinElmer, Wellesley, Mass.). Pyrolysis was performed at 1,400° C. for 30 s, and atomization was performed at 2,200° C. for 5 s.

MRI samples prepared as described above were arrayed into microtiter plates and placed in a 40-cm-bore Avance 4.7 T MRI scanner (Bruker, Billerica, Mass.). Unused wells were filled with PBS, and imaging was performed on a 2-mm slice through the sample. A spin echo pulse sequence with multi-echo acquisition was used. The TR was fixed for every acquisition, and the TE was in defined increments. For example, for TR=100 ms, TE varied from 10 to 80 ms, with a 10-ms increment. To adjust further the weight between T1 and T2, various TRs were applied and the TE increment was changed accordingly, if necessary. Data matrices of 512×128 points were acquired and zero-filled to 256 points in the second (phase encoding) dimension. Images were reconstructed and analyzed by using custom routines running in Matlab (Mathworks, Natick, Mass.).

Example 1

The following example describes the synthesis of 2,2'-(phenylmethylene)bis(1H-pyrrole) (compound 3). A solution containing 200 mL of $H_2O$ and 50 mL of pyrrole (0.72 mol) was prepared and bubbled with argon for 15 min. A 1-mL portion of HCl (37% aq.) was added, followed by benzaldehyde (14.2 mL, 0.14 mol) in a dropwise manner over 15 min. The solution turned brown and was maintained under argon for an additional 2 h, after which it was carefully neutralized with $NH_4OH$ and then diluted with 100 mL of $H_2O$ and extracted with $CH_2Cl_2$ (3×150 mL). The combined organic phases were dried over $Na_2SO_4$ and allowed to evaporate to remove solvent and excess pyrrole. The resulting solid mixture was dissolved in 100 mL of toluene at 80° C. and slowly cooled to room temperature to yield a first crop of product (11.0 g white powder) by filtration. The mother liquor was further concentrated to yield two more batches of product with acceptable purity. A total of 17.1 g of pure material was isolated as a pale white solid, yield 55%. Mp 100.3-101.4° C. [mp 102.0-102.5° C., as reported in Lippard et al., *Principles of Bioinorganic Chemistry*, University Science Books: Mill Valley, Calif., 1994]. $^1$H NMR ($CD_2Cl_2$, 400 MHz) δ: 5.51 (1H, s), 5.95 (2H, br. s), 6.19 (2H, dd, J1=6.0 Hz, J2=2.6 Hz), 6.72 (2H, m), 7.24~7.37 (5H, m). $^{13}$C NMR ($CD_2Cl_2$, 100.6

MHz) δ: 44.4, 107.7, 108.9, 117.7, 127.4, 128.8, 129.1, 132.9, 142.5. ESI-MS Calcd. M–H⁻, 221.1. Found, 221.4.

Example 2

The following example describes the synthesis of 5-(2,6-N-dinitrophenyl)-10,15,20-trisphenylporphyrin ($2NO_2$-TPP) (compound 4). (Phenylmethylene)bis(1H-pyrrole) (3, 3.112 g, 14.0 mmol), freshly distilled benzaldehyde (712 µL, 7.0 mmol), and 2,6-dinitrobenzaldehyde (1.575 g, 8.0 mmol) were dissolved in a liter of dry $CH_2Cl_2$ under argon. A 1-mL portion of BF3.Et2O was injected into the reaction solution, which was then stirred at room temperature for 2 h in the dark. 2,3-Dichloro-5,6-dicyano-1,4-benzoquinone (DDQ) (6.8 g, 30 mmol) was added and the reaction was allowed to proceed under argon in the dark overnight. The solvent was removed and the resulting solid residue was dissolved in $CH_2Cl_2$/MeOH (3:1) and then mixed with aluminum oxide (~80 g). The mixture was evaporated to dryness. Flash chromatography using an aluminum oxide column, followed by passage through a second, silica gel column afforded 569.0 mg of a purple solid. Yield: 11.5%. ¹H NMR ($CD_2Cl_2$, 400 MHz) δ: 2.73 (2H, s, br), 7.83 (9H, m), 8.22 (1H, t, J=8.3 Hz), 8.26 (6H, m), 8.55 (2H, d, J=8.3 Hz), 8.70 (2H, d, J=4.7 Hz), 8.89 (4H, s, br), 8.93 (2H, d, J=4.7 Hz). ESI-MS Calcd. M+H⁺, 705.2. Found, 705.2. UV-vis ($CH_2Cl_2$, nm) 419 ($\lambda_{max}$ Soret band), 518, 551, 593 (Q-bands). FTIR (KBr, cm⁻¹) 3317 (w), 3055 (w), 2920 (w), 1535 (s, σNO), 1350 (s, σNO), 965 (s), 800 (s), 729 (m), 703 (s).

Example 3

The following example describes the synthesis of 5-(2,6-diaminophenyl)-10,15,20-trisphenylporphyrin ($2NH_2$-TPP) (compound 5). A mixture of $2NO_2$-TPP, (4, 98.4 mg) and $SnCl_2$ (390.1 mg) was stirred in 5 mL of 1 N aqueous HCl under argon in the dark at room temperature for 12 h and cooled in an ice bath. The solution was then carefully titrated with $NH_4OH$ until the color of mixture changed from green to brown at pH 10. The mixture was diluted with 50 mL of water and extracted with $CH_2Cl_2$ (3×50 mL). The organic layer was washed with water and brine and then dried over $Na_2SO_4$. The solvent was removed and the residue was purified by silica gel column chromatography using a gradient eluent from $CH_2Cl_2$/hexan (4:1) to $CH_2Cl_2$/ethyl-acetate (6:1); 77.0 mg of product was obtained as a purple solid (85.5%). ¹H NMR ($CD_2Cl_2$, 400 MHz) δ: 2.75 (2H, s), 3.39 (4H, s, br), 6.64 (2H, d, J=8.1 Hz), 7.43 (1H, t, J=8.1 Hz), 7.83 (9H, m), 8.27 (6H, dd, J1=7.5 Hz, J2=1.5 Hz) 8.90 (4H, s), 8.92 (2H, d, J=5.1 Hz), 9.03 (2H, d, J=5.1 Hz). ESI-MS Calcd. M+H⁺, 645.3. Found, 645.2. UV-vis ($CH_2Cl_2$, nm) 417 ($\lambda_{max}$ Soret band), 514, 549, 591 (Q-bands). FTIR (KBr, cm⁻¹) 3462 (w, σNH), 3372 (w, σNH), 3318 (w, σNH), 1607 (s, $NH_2$ deformation), 1595 (s, $NH_2$ deformation), 1557 (m), 1466 (s), 1441 (m), 1348 (m), 1001 (m), 978 (m), 964 (s), 773 (s), 732 (s), 701 (s).

Example 4

The following example describes the synthesis of 5-(2,6-diaminophenyl)-10,15,20-tris(3-sulfonatephenyl)porphyrin ($2NH_2$-$TPPS_3$) (compound 6). Solid $2NH_2$-TPP (5, 86 mg) was suspended in 3 mL of concentrated. sulfuric acid (95.8%), and the flask was placed in an ultrasonic bath for 1 min to homogenize the mixture. The solution was heated in an oil bath at 80° C. for 72 h. The reaction was allowed to stir at room temperature for 24 h, cooled in an ice bath, diluted with 10 mL of $H_2O$, and neutralized with a 3 M NaOH solution until pH 8, during which the color changed from green to red. The water was evaporated and the solid residue washed with MeOH. The MeOH solution was concentrated and purified by reverse-phase chromatography, using an $H_2O$/MeOH gradient (from 100% $H_2O$ to 60% $H_2O$). A reddish purple solid was obtained. (77 mg, 65.3%). ¹H NMR (DMSO-d6, 400 MHz) δ: 2.80 (2H, s), 4.11 (4H, s, br), 6.46 (2H, d, J=7.7 Hz), 7.22 (1H, t), 8.06 (6H, d), 8.19 (6H, d), 8.84 (6H, s, br), 8.93 (2H, s, br). ESI-MS Calcd M–H⁻, 883.1, [½](M-2H⁻²) 441.1. Found, 882.6, 442.6. UV-vis ($H_2O$, nm) 431 ($\lambda_{max}$ Soret band), 466, 486.

Example 5

The following example describes the synthesis of (DPA-$C_2$)$_2$-$TPPS_3$ (compound 1). A mixture of $2NH_2$-$TPPS_3$ (5, 10.6 mg, 12 µmol), 4-hydroxy-2-pyridin-2-ylmethyl-1,2,3,4-tetrahydro-pyrido[1,2-a]pyrazin-5-ylium dichloride, (7, 9.4 mg, 30 µmol), and freshly powdered dry $Na_2SO_4$ (97.6 mg 0.687 mmol) in 2 mL of dry methanol was stirred at room temperature for 2 h. A portion of $NaCNBH_3$ (3.2 mg, 50.9 µmol) was added and the reaction was allowed to stir for 3 h. The course of the reaction was followed by ESI-MS and TLC. After filtration, the solvent was evaporated and the residue was purified on a reverse phase (RP-18) column chromatograph, using as eluent water to water/MeOH (5/4) to yield, after evaporation, a red/purple solid (9.1 mg, 56.8%). ¹H NMR (DMSO-d6, 400 MHz) δ-2.9 (2H, br), 3.03 (4H, br) 3.37 (4H, br), 3.98 (10H, m), 6.55 (2H, d), 6.84 (8H, m) 7.33 (4H, m), 7.45 (1H, m), 7.76 (4H, d), 8.05 (10H, m), 8.19 (2H, d), 8.63 (2H, m), 8.85 (6H, m). ESI-MS Calcd M–H-1333.4, [½](M-2H)²⁻ 666.2. Found 1333.9, 666.5; UV-vis ($H_2O$, nm) 421 ($\lambda_{max}$), 468, 486.

Example 6

The following example describes the synthesis of (DPA-$C_2$)$_2$-Mn(III)$TPPS_3$ (compound 2). Portions of (DPA-$C_2$)$_2$-$TPPS_3$ (1, 6.5 mg, 4.87 µmol) and Mn(II) acetate (9.8 mg, 56.6 µmol) were dissolved in 2 mL of anhydrous DMF and heated to 90° C. for 6 h. The reaction course was followed by UV-visible spectroscopy. The starting material had a $\lambda_{max}$ of 421 nm, whereas the product absorbed at 467 nm. Consequently, the color of the solution turned from dark red to dark green after 6 h. Evaporation of DMF gave a residue that was purified by reverse-phase column chromatography using a $H_2O$/MeOH gradient (0% MeOH to 60% MeOH). A 1.5-mg quantity of (yield 22%) product (dark-green solid) was obtained. ESI-MS Calcd [½](M-3H)²⁻ 692.1, ⅓ (2M-5H)³⁻ 923.2. Found 692.8, 923.8. UV-vis ($H_2O$) 467 nm. X-band EPR indicated that the product was free from Mn(II).

Example 7

The following example describes the spectroscopic properties of (DPA-$C_2$)$_2$-$TPPS_3$ (compound 1) and its use as a fluorescent zinc(II) sensor, wherein the DPA group functions as a binding moiety for zinc ions.

Figure 5:
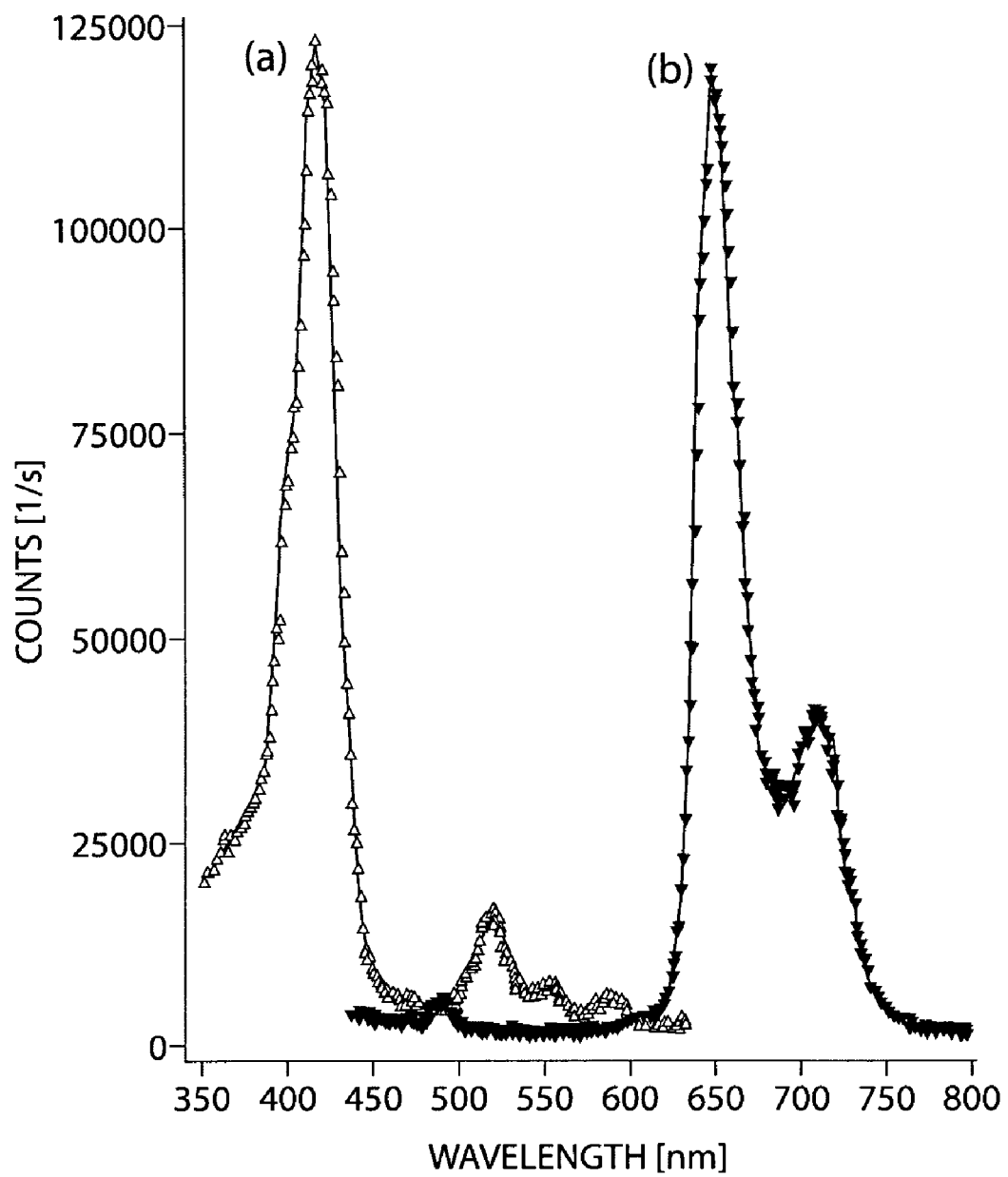
FIG. 5 shows the (a) excitation and (b) emission spectra of 5 μM $(DPA-C_2)_2-TPPS_3$ (compound 1).

The spectroscopic properties of compound 1 were evaluated in buffered neutral aqueous solution (50 mM Hepes/100 mM KCl, pH 7.0). FIG. 5 shows the (a) excitation and (b) emission spectra of 5 µM compound 1. The spectra were acquired in 50 mM Hepes/100 mM KCl at pH 7.0. Excitation was provided at 418 nm for the emission spectrum, and emission was detected at 648 nm for the excitation spectrum. In the absorption spectrum, compound 1 exhibited a Soret band centered at 416 nm with a high extinction coefficient (ε=250, 700 M$^{-1}$·cm$^{-1}$). Upon excitation at this wavelength, two emission bands in the far red (648 nm, strong) and near-IR (715 nm, medium) regions were observed. The large Stokes shift ((230 nm) observed for compound 1 may be advantageous for fluorescence imaging, as a small Stokes shift can cause self-quenching and measurement error due to noise from the excitation and scattered light. Moreover, because compound 1 exhibited an emission at relatively long wavelengths, interference caused by absorption and autofluorescence by biomolecules can be reduced, facilitating imaging at deeper penetration depths in tissues.

Figure 6:
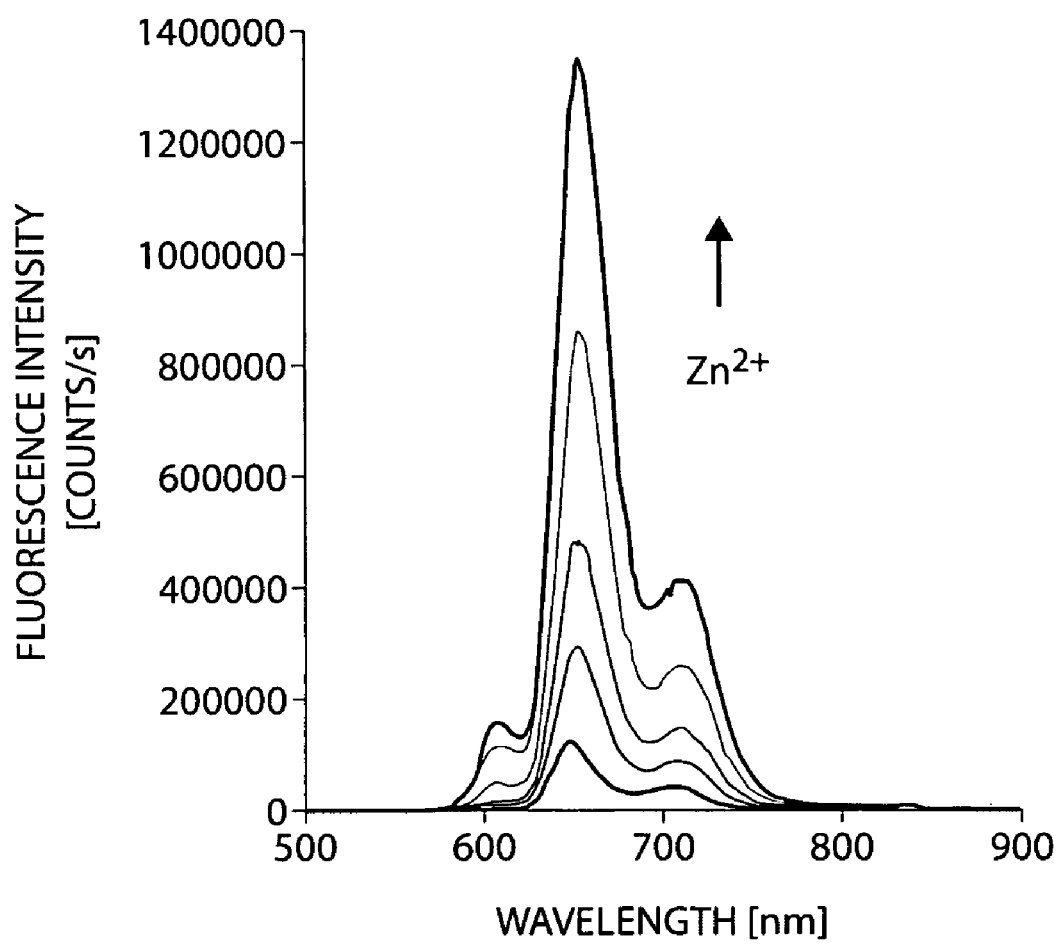
FIG. 6 shows the fluorescence emission spectra of 5 μM $(DPA-C_2)_2-TPPS_3$ upon addition of various amounts of $Zn^{2+}$.

FIG. 6 shows the fluorescence spectroscopic response of 5 (M compound 1 upon stepwise addition of Zn$^{2+}$. Spectra were acquired in 50 mM Hepes/100 mM KCl at pH 7.0, and the excitation was provided at 418 nm. Appropriate aliquots of a ZnCl$_2$ stock solution in pure water were added to achieve the total zinc concentration [Zn$^{2+}$]$_t$. The spectra shown in FIG. 6 represent the spectra for [Zn$^{2+}$]$_t$ of 0, 1, 2.5, 3.5, 5 (saturation point), 7.5, 10, and 20 μM. The fluorescence emission of compound 1 was observed to be relatively dim in the absence of zinc. The measured quantum yield was 0.004 (TPPS$_4$ as reference) for a 5 mM solution of 1 in 50 mM Hepes buffer (pH 7.0), 100 mM KCl. Upon the addition of zinc(II) chloride to this solution, the fluorescence intensity increased significantly. In the zinc-saturated form, the quantum yield was measured to be 0.046, >10 times greater than that of the zinc-free form (FIG. 6). A nonlinear least-squares fit of the zinc fluorescence titration data returned a K$_d$ value of 12 nM for the formation of a 1:1 complex between 1 and zinc. As shown for ZP1 and its derivatives, which also contain two zinc-binding sites, the second zinc-binding event was fluorescence-insensitive.

Figure 7:
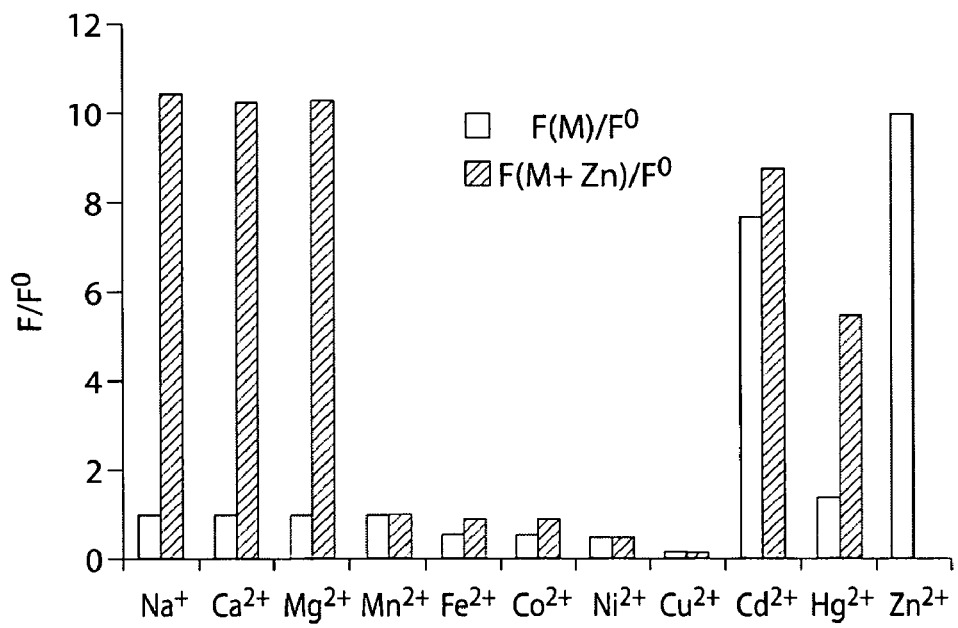
FIG. 7 shows a graph of the fluorescence emission intensity of $(DPA-C_2)_2-TPPS_3$ in the presence of various metal ions.

Compound 1 was then exposed to various metal ions, to evaluate the selectivity of compound 1 for zinc ions. A range of metal ions were supplied as chloride salts, except for Fe(II) and Cu(II), which were added as (NH$_4$)2Fe(SO$_4$)$_2$.6H$_2$O and CuSO$_4$.5H$_2$O, respectively, and spectra were acquired in 50 mM Hepes/100 mM KCl at pH 7.0. FIG. 7 shows the fluorescence spectroscopic responses of compound 1 to the various metal ions, wherein the bars represent the ratio of fluorescence intensities before and after the addition of the corresponding metal ions. The open bars represent the addition of an excess of the appropriate metal ion (100 (M) to a 5-(M solution of compound 1, and filled bars represent the subsequent addition of 100 (M Zn2+ to the solution. Excitation was provided at 418 nm.

The fluorescence "turn-on" of compound 1 was selective for Zn$^{2+}$ over many other monovalent and divalent metal ions (FIG. 7). Even large excesses of Na$^+$, K$^+$, Ca$^{2+}$, and Mg$^{2+}$, which are biologically relevant, potentially competing, mobile metal ions, barely perturb the fluorescence of the zinc-free and zinc-bound forms of compound 1. Various divalent first-row transition metal ions, including Mn$^{2+}$, Fe$^{2+}$, Co$^{2+}$, Ni$^{2+}$, and Cu$^{2+}$, were observed to quench the fluorescence of compound 1. Although Cd$^{2+}$ and Hg$^{2+}$ can "turn on" the fluorescence of compound 1 to a certain degree, neither is significantly abundant in typical biological samples.

Figure 8:
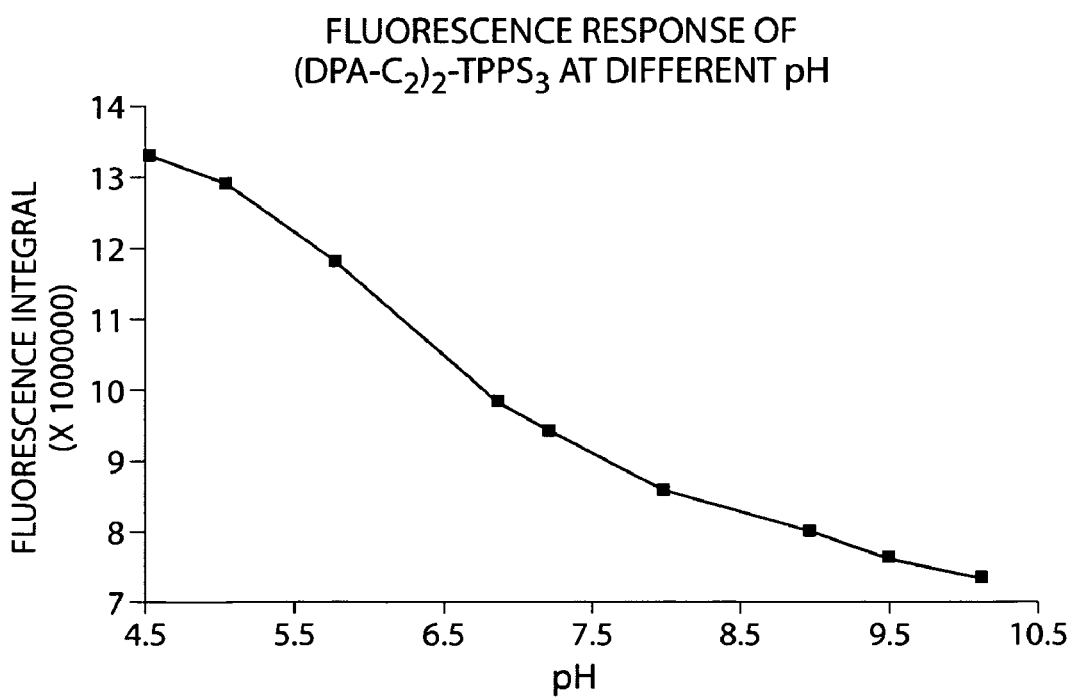
FIG. 8 shows the fluorescence pH profile of 5 μM of compound 1 in 100 mM KCl solution.

The pH-sensitivity of compound 1 was then studied. In some cases, it may be advantageous to reduce fluorescence turn-on by protonation for fluorescent zinc(II) sensors, as protonation can diminish the sensitivity of the sensor to zinc by increasing the background signal intensity. FIG. 8 shows the fluorescence pH profile of 5 μM of compound 1 in 100 mM KCl solution. The pH values of the solution were adjusted by adding an appropriate volume of HCl or KOH stock solution. The fluorescence spectrum was measured upon excitation at 416 nm, and the fluorescence intensity was integrated from 550 to 800 nm. Relative to some known zinc sensors, the fluorescence response of compound 1 was observed to be much less pH-sensitive within the biologically relevant window. A fluorescence increase of less than a factor of two occurred as when the solution acidity was increased (pH 10.1 to pH 4.5).

Example 8

The following example describes the use of compound 1 in intracellular imaging of zinc by fluorescence microscopy. Compound 1 was shown to by membrane-permeable in all cell lines tested. For this study, HEK-293 was selected as the cell line for demonstration of fluorescence imaging. Suspension cultures of HEK-293 enabled production of a sizeable cell pellet, which was then plated as an adherent monolayer for fluorescence imaging studies. The monolayer cultures were subcultured five times after the initial plating, grown to 70% confluence on glass cover slips and treated with compound 1 for fluorescence imaging. The cytotoxicity of compound 1 was evaluated in these adherent HEK-293 cells by incubating them with 5 μM of compound 1 for 24 h. These cells were healthy as compared with control, untreated cells according to cell counting and viability analysis using trypan blue.

Figure 9:
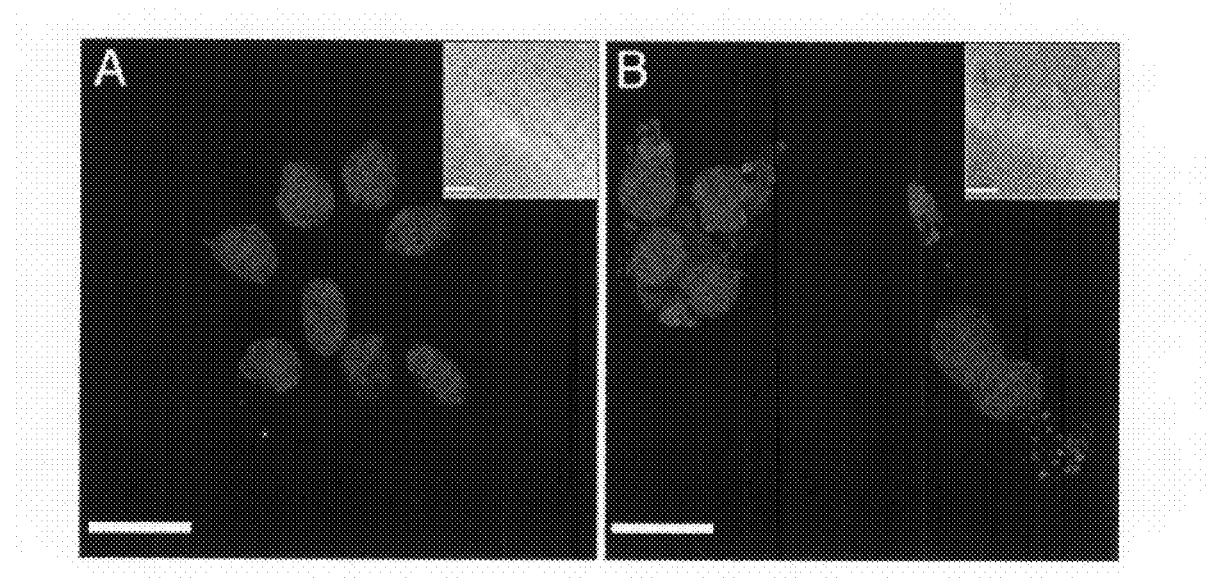
FIG. 9 shows fluorescence microscopy images of (a) cells without addition of exogenous zinc and (b) cells incubated with 40 μM $Zn^{2+}$ carried by the ionophore pyrithione (1:1) for 10 min before fixing, wherein the insets show the corresponding bright-field images.

Fixed cells were investigated by fluorescence imaging using a customized optical filter (exciter: D425/50; emitter: E6001p; beamsplitter: 460dcxr), which was designed to match the excitation and emission profiles of compound 1. The cell nuclei were costained with the blue fluorescent dye Hoechst 33258 (0.4 μM). The HEK-293 cells were incubated with 5 μM of compound 1 for 24 h before fixing. FIG. 9 shows fluorescence microscopy images of (a) cells without addition of exogenous zinc and (b) cells incubated with 40 μM Zn$^{2+}$ carried by the ionophore pyrithione (1:1) for 10 min before fixing. The insets show the corresponding bright-field images (Scale bars: 25 μm). The treated cells showed faint red fluorescence from compound 1, and a significant increase in the red fluorescence intensity occurred upon the addition of Zn$^{2+}$ (40 μM) carried by the ionophore pyrithione (2-mercaptopyridine-N-oxide), as shown in FIG. 9B, indicating that compound 1 was taken up by the cell and the intracellular Zn$^{2+}$ can be detected by fluorescence turn-on of compound 1. Thus, compound 1 was shown to be a valuable zinc fluorescence sensor and can be useful for intracellular zinc imaging.

Example 9

The following example describes the synthesis and MRI properties of (DPA-C$_2$)$_2$-TPPS$_3$Mn(III) (compound 2) and its use as a zinc(II) MRI sensor, wherein the DPA group functions as a binding site for zinc ions.

Insertion of a paramagnetic manganese(III) ion into the porphyrin core of compound 1 rendered the resulting (DPA-C$_2$)$_2$-TPPS$_3$Mn(III) complex (compound 2) an MRI contrast agent. The properties of compound 2 were investigated by using a spin echo pulse sequence to collect images at several echo times (TEs) in parallel. In some experiments, the repetition times (TRs) were varied so that both T1 and T2 could be evaluated. Multiwell plates were used for sample preparation, which allowed several conditions to be investigated in parallel. The well-studied MRI T1 agent, Mn-TPPS$_4$, which contains a similar porphyrin platform as compound 2 but lacks a zinc-binding unit, was chosen as a reference compound.

Figure 10:
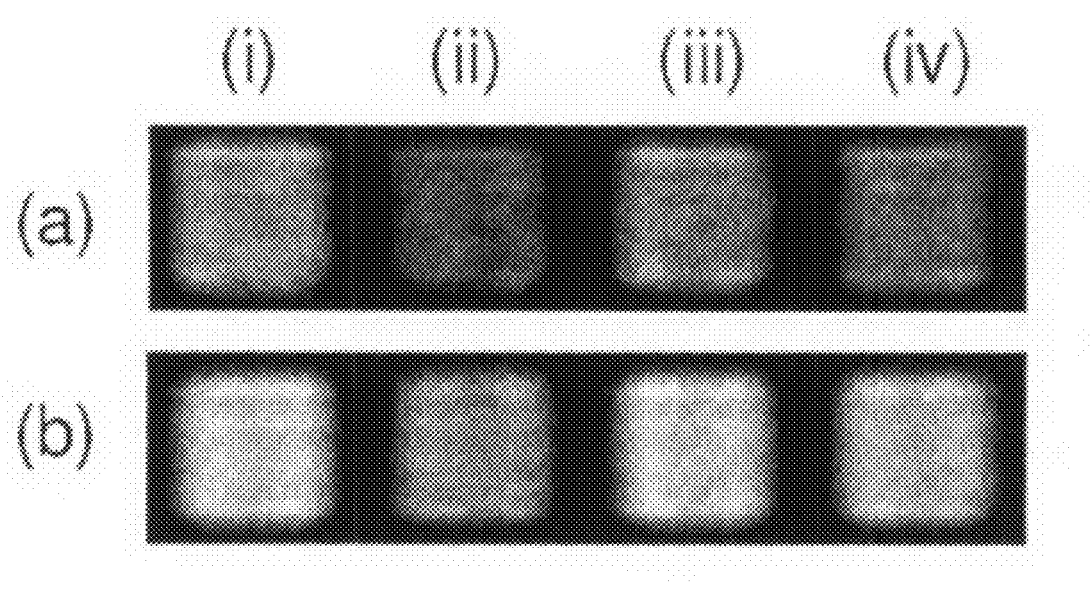
FIG. 10 shows (a) T1-weighted images (TR=175 ms; TE=10 ms; 200 μM contrast agent) and (b) T2-weighted images (TR=2,000 ms; TE=240 ms; 500 µM contrast agent with 100 mM KCl) for the $Zn^{2+}$-induced relaxation rate change in buffered solution, as measured by MRI, for (i) $(DPA-C_2)_2$-$TPPS_3Mn(III)$ without zinc, (ii) $(DPA-C_2)_2$-$TPPS_3Mn(III)$ with 1 mM $Zn^{2+}$, (iii) Mn-$TPPS_4$ without zinc, and (iv) Mn-$TPPS_4$ with 1 mM $Zn^{2+}$.

The zinc-dependent MR relaxivity of compound 2 was first investigated in buffered solutions. Solutions of compound 2 or Mn-TPPS$_4$ in 25 mM Pipes buffer at pH 7.0 were arrayed in microtiter plates. A spin echo pulse sequence was used to acquire an MRI image. FIG. 10 shows (a) T1-weighted images (TR=175 ms; TE=10 ms; 200 μM contrast agent) and (b) T2-weighted images (TR=2,000 ms; TE=240 ms; 500 μM contrast agent with 100 mM KCl) for the Zn$^{2+}$-induced relaxation rate change in buffered solution, as measured by MRI, for (i) compound 2 without zinc, (ii) compound 2 with 1 mM Zn$^{2+}$, (iii) Mn-TPPS$_4$ without zinc, and (iv) Mn-TPPS$_4$ with 1 mM Zn$^{2+}$. Addition of 1 mM ZnCl$_2$ to a 200 μM solution of compound 2 dissolved in 25 mM Pipes buffer at pH 7 slowed down the T1 relaxation. The solutions containing compound 2 showed that the presence of zinc lowers the MR signal intensity in both the T1-weighted and T2-weighted images. As shown in FIG. 10A, the well containing compound 2 and zinc was less bright (e.g., had lower signal intensity) than the well containing compound 2 without zinc. By comparison, almost no change occurred upon addition of zinc to the reference solution of Mn-TPPS$_4$. The T1 values of zinc-free and zinc-saturated solutions were determined at various concentrations of compound 2, from which T1 relaxivity (R1) values could be deduced. The R1 of the zinc-free form of 2 was 8.7 mM$^{-1}$·s$^{-1}$, which decreased to 6.65 mM$^{-1}$·s$^{-1}$ upon formation of the zinc complex.

Figure 11A:
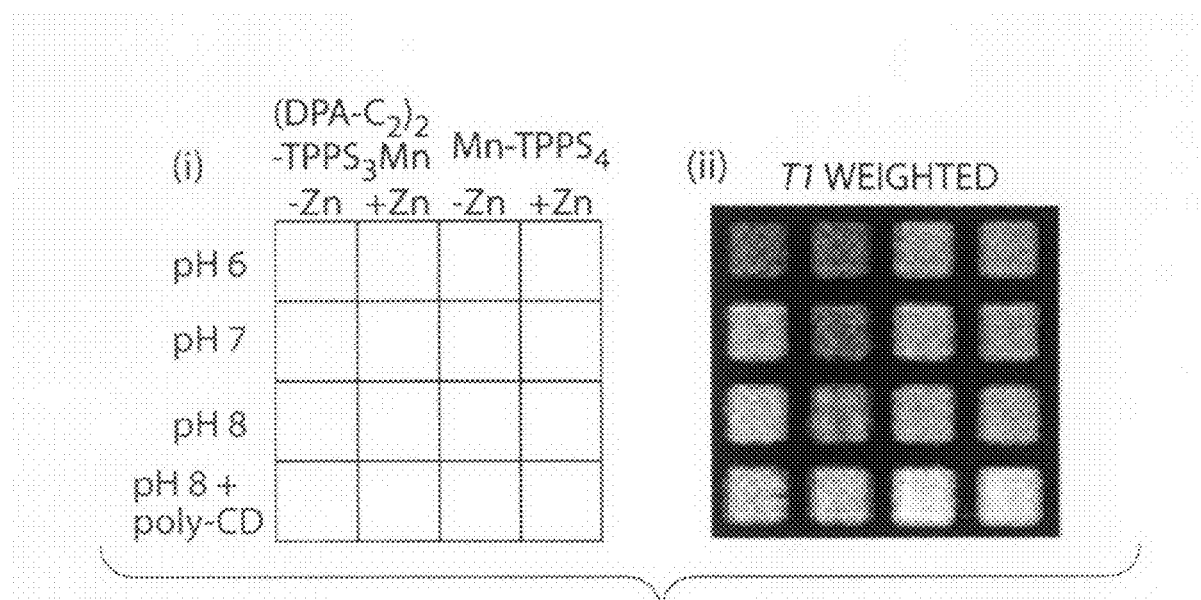
FIG. 11A shows (i) a schematic representation of the experimental setup and individual conditions for samples of $(DPA-C_2)_2$-$TPPS_3Mn(III)$, and (ii) T1-weighted images of the samples upon changes in pH and/or addition of poly-β-cyclodextrin ("poly-CD").
Figure 11B:
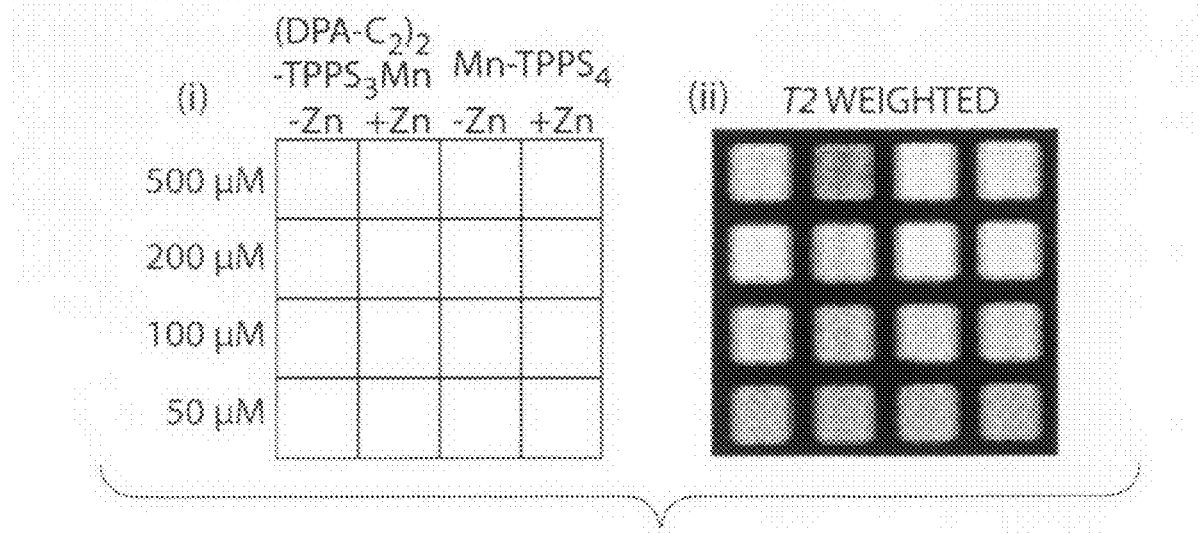
FIG. 11B shows (i) a schematic representation of the experimental setup and individual conditions for samples of $(DPA-C_2)_2$-$TPPS_3Mn(III)$, and (ii) T2-weighted images of the samples upon addition of different amounts of $(DPA-C_2)_2$-$TPPS_3Mn(III)$.

Further studies revealed that the zinc-induced relaxivity change of compound 2 in solution was affected by various conditions, such as pH and ionic strength. FIG. 11A shows (i) a schematic representation of the experimental setup and individual conditions for each sample, and (ii) T1-weighted images of the samples upon changes in pH and/or addition of poly-β-cyclodextrin ("poly-CD"). FIG. 11B shows (i) a schematic representation of the experimental setup and individual conditions for each sample, and (ii) T2-weighted images of the samples upon addition of different amounts of compound 2. The surrounding wells (not shown) were filled with PBS to maintain a homogenous magnetic field to mark the positions of the samples.

As shown in FIG. 11A, the zinc-induced T1 contrast was more significant at pH 7 than at pH 6 or 8 and is significantly diminished at high ionic strength (100 mM KCl). Instead of a T1 relaxation change at high ionic strength, a zinc-induced enhancement of T2 relaxation was observed. As shown in FIG. 11B, the solutions with zinc showed a lower signal intensity than that of the zinc-free sample. The reference Mn-TPPS$_4$ displayed no zinc-induced T2 change. Notably, unlike the T1 effect, an increase in the T2 relaxation rate reduced the MR signal intensity. The zinc-induced T2 enhancement depended on the total concentration of compound 2.

Example 10

Figures 12A, 12B:
FIG. 12 shows photographs of pellets of (a) HeLa cells incubated with 100 µM $(DPA-C_2)_2$-$MnTPPS_3$ for 24 h and (b) blank control cells, wherein the darker-colored pellet indicates cellular uptake of $(DPA-C_2)_2$-$TPPS_3Mn(III)$.

The following example describes the study of compound 2 for cellular MR imaging. For this study, HEK-293 was selected as the cell line for demonstration of MR imaging using compound 1. Suspension cultures of HEK-293 enabled production of a sizeable cell pellet suitable for MRI studies. After a 24-h incubation of HEK-293 cells with 100 μM2, the cell density was similar to that of untreated control cells, indicating that compound 2 has little cytoxicity. Centrifugation and washing with PBS yielded a dark-green cell pellet, a color typical of manganese porphyrins, indication that compound 2 either accumulated intracellularly or became associated with the cell membrane. By comparison, the control cell pellet was pale white. To further illustrate, an analogous experiment was conducted for HeLa cells, and similar results were obtained. FIG. 12 shows photographs of pellets of (a) HeLa cells incubated with 100 μM (DPA-C$_2$)$_2$-MnTPPS$_3$ for 24 h and (b) blank control cells, wherein the darker-colored pellet indicates cellular uptake of compound 2.

To confirm the membrane permeability and further investigate the subcellular localization of compound 2, the cells were lysed, and nuclear and cytosolic fractions were extracted and analyzed by atomic absorption spectroscopy (AAS). The results indicated that compound 2 is cell membrane-permeable and preferentially localizes in the nuclear fractions (5.62 mg Mn/liter), rather than in the cytosol (0.78 mg Mn/liter). By contrast, no Mn AAS signal was observed in the control cells.

To investigate zinc-induced relaxivity changes in compound 2 inside cells, cell pellets were prepared with and without exogenously introduced zinc, and their MR images were recorded and compared. The HEK-293 cell suspension was divided equally into two flasks after a 24-h treatment with 100 μM of compound 2 or Mn-TPPS$_4$. A 200-μM portion of zinc pyrithione was then added to one of the samples and incubated for an additional 10 min. As in the solution studies, comparisons were made by using Mn-TPPS$_4$ as a reference compound. In addition, an untreated cell sample was prepared as a control. The cell suspensions were pelleted by centrifugation, washed, and transferred into a multiwell plate for MRI analysis. A spin echo pulse sequence was used to acquire MRI images.

Figure 13A:
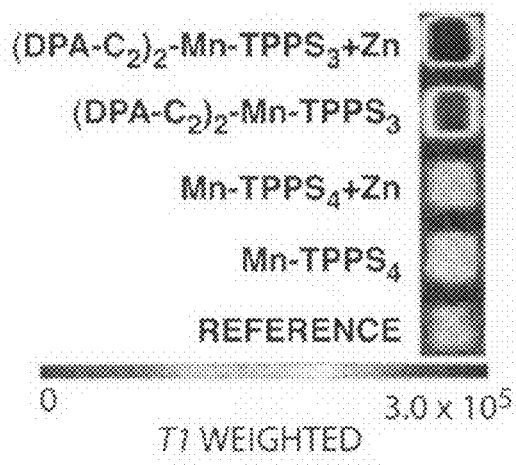
FIG. 13 shows (a) the T1-weighted MR images for intracellular zinc in HEK-293 cells and (b) the measurement of zinc-induced T1 changes by MRI.
Figure 13B:
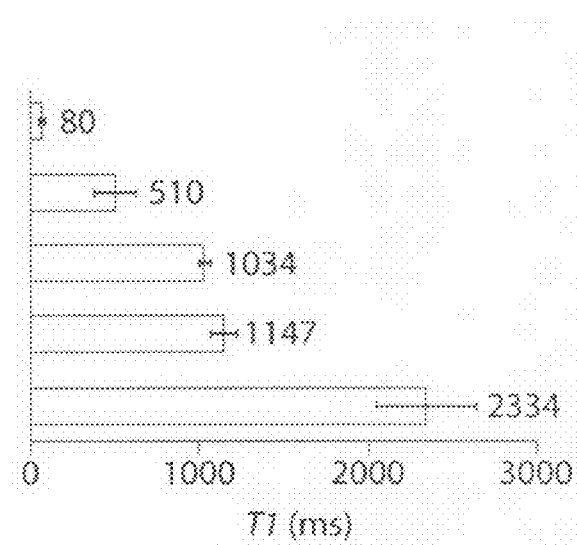
Figure 14A:
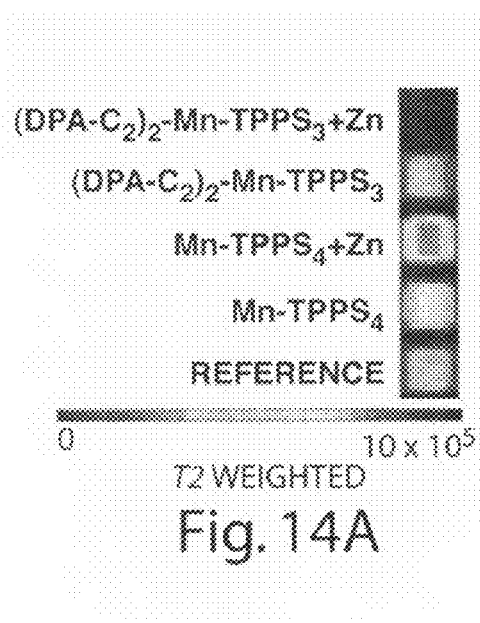
FIG. 14 shows (a) the T2-weighted MR images for the intracellular zinc in HEK-293 cells and (b) the measurement of zinc-induced T2 changes by MRI.
Figure 14B:
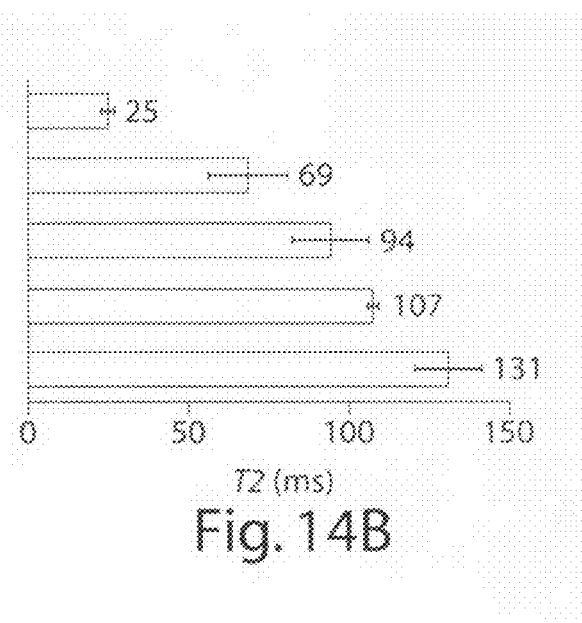

FIG. 13 shows (a) the T1-weighted MR images for the intracellular zinc in HEK-293 cells and (b) the measurement of zinc-induced T1 changes by MRI. FIG. 14 shows (a) the T2-weighted MR images for the intracellular zinc in HEK-293 cells and (b) the measurement of zinc-induced T2 changes by MRI. T1 and T2 were determined by a series of MR images with varied TR or TE, respectively. The values reported are the average from three separate experiments with standard deviations as indicated by the horizontal bars.

As shown in FIG. 13, cells incubated with compound 2 or Mn-TPPS$_4$, either with or without zinc, exhibited, to differing degrees, increased MR signal intensities compared with that of the untreated control cell samples in the T1-weighted image (TR=100 ms; TE=10 ms). The increased MR signal intensity in the treated samples indicates that both contrast agents are taken up by the cells. From the relative increase in signal intensities, compound 2 exhibited greater cell membrane permeability than Mn-TPPS$_4$.

Comparing the two cell samples that had been incubated with compound 2, a significantly greater MR signal intensity in the T1-weighted image (TR 100 ms; TE 10 ms) was observed for cells treated with exogenous zinc than for untreated cells. Consequently, the determined T1 value for the zinc-containing sample (T1=80 ms) was significantly shorter than that of the zinc-free sample (T1=510 ms). By comparison, there was no obvious difference between the two MnTPPS$_4$-treated cell samples in the presence or absence of zinc (T1=1.0 and 1.1 s, respectively). The T1 is represented as a bar at the right side of the adjacent corresponding sample in FIG. 13B (same for the T2 value in FIG. 14B). By increasing the TE from 100 to 2,000 ms, and the TR from 10 to 120 ms, a T2-weighted MRI image was obtained for the same sample.

Figure 15:
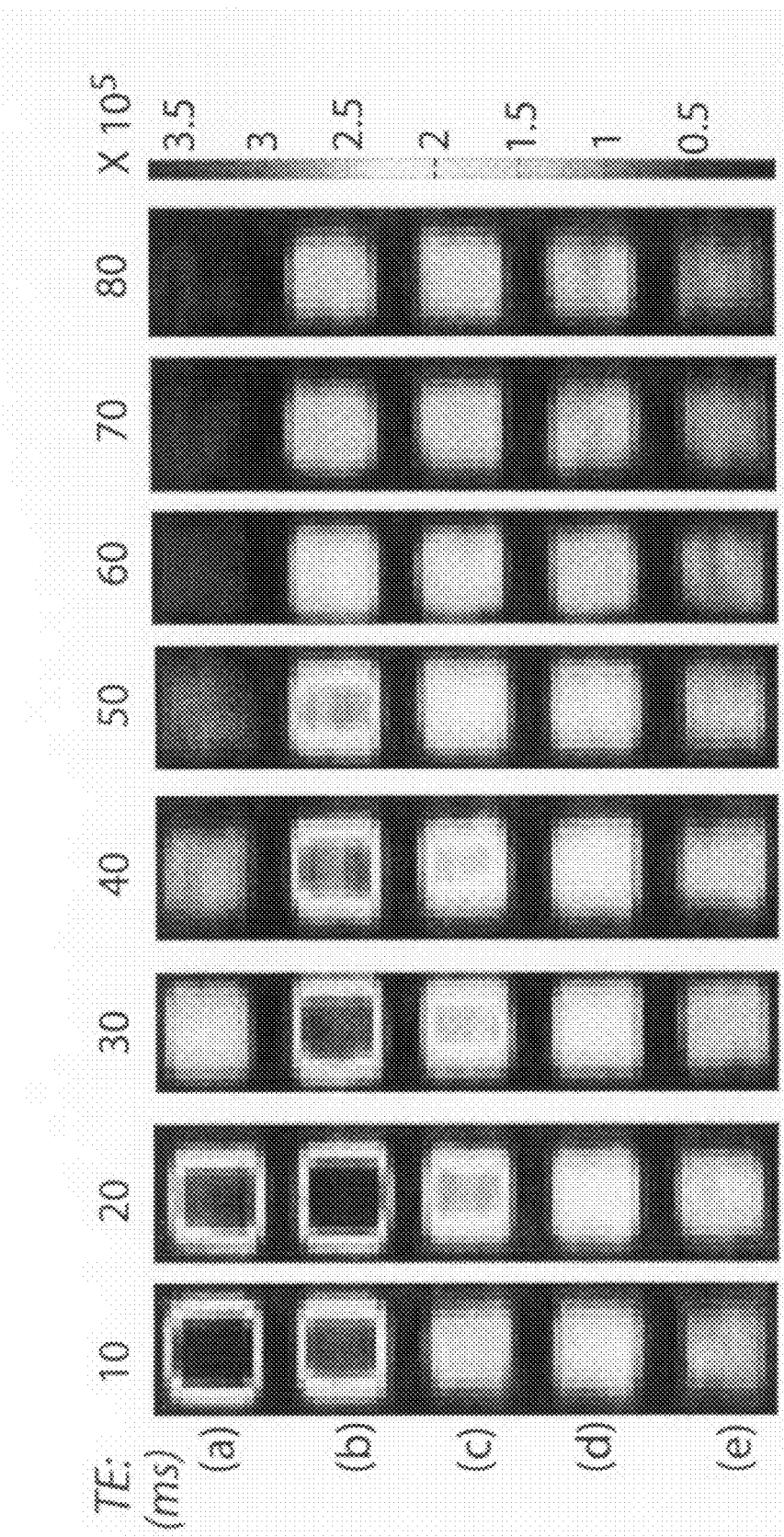
FIG. 15 shows a series of images of the cell pellets recorded with fixed TR (100 ms) and variable TE, from 10 to 80 ms in 10-ms increments, for wells containing cells incubated with (a) 100 µM of compound 2 for 24 h followed by addition of 200 µM $Zn^{2+}$, (b) 100 µM of compound 2 for 24 h without exogenous zinc, (c) 100 µM Mn-$TPPS_4$ for 24 h followed by addition of 200 µM $Zn^{2+}$, (d) Mn-$TPPS_4$ for 24 h without exogenous zinc, and (e) control reference cells for 24 h.

As shown in FIG. 14, for both cell pellets treated with compound 2, the T2-weighted image (TR 2,000 ms; TE 120 ms) of the sample containing exogenous zinc showed a significantly lower signal intensity than that of the untreated sample, indicating a zinc-induced enhancement of the T2 effect. To further demonstrate the T2 effect of intracellular zinc-induced MR relaxivity change in HEK-293 cells, FIG. 15 shows a series of images of the cell pellets recorded with fixed TR (100 ms) and variable TE, from 10 to 80 ms in 10-ms increments, for wells containing cells incubated with (a) 100 μM of compound 2 for 24 h followed by addition of 200 μM $Zn^{2+}$, (b) 100 μM of compound 2 for 24 h without exogenous zinc, (c) 100 μM Mn-TPPS$_4$ for 24 h followed by addition of 200 μM $Zn^{2+}$, (d) Mn-TPPS$_4$ for 24 h without exogenous zinc, and (e) control reference cells for 24 h. The surrounding wells (not shown) were filled with PBS to keep the magnetic field homogeneous in the center. The MR images were recorded by using a spin echo pulse sequence with TR=100 ms and multiple TE values ranging from 10 to 80 ms as marked.

As shown in FIG. 15, for cells incubated with compound 2 and $Zn^{2+}$, the signal intensity decreased rapidly upon an increase of TE, revealing the zinc-induced T2 effect. The T2 value determined from the zinc-treated samples was 25.0 ms, which is significantly shorter than the T2 of the non zinc-treated samples (69 ms). For Mn-TPPS$_4$ samples, the zinc-induced T2 effect was not significant (T2=107 ms without zinc, 94 ms with zinc).

The enhancement in relaxivity of compound 2 with added zinc in cells demonstrated that compound 2 can function as a cell-permeable MRI sensor for detecting intracellular zinc in both T1- and T2-weighted images.

Example 11

The following example describes the synthesis of BAPTA-TEF, a binding moiety for calcium ions. (FIG. 17) BAPTA-Et$_4$ (224.2 mg) was dissolved in 1 mL dry DMF, and 50 μL POCl$_3$ was slowly added dropwise. The color of the solution changed to red, and the reaction was heated to 110° C. for 4.5 hours, and then cooled down to room temperature. The reaction mixture was then stirred at room temperature overnight. The resulting solution was poured into 15 mL 10% NaOAc aqueous solution at 0° C. and stored in a refrigerator overnight, and a solid precipitate formed. The solution phase was decanted from the solid, and the solid was dissolved in $CH_2Cl_2$ and dried over $Na_2SO_4$. The solution was filtered and the solvent was removed. The remaining residue was purified by silica gel column chromatography, using ethyl acetate:toluene (20:80) as eluant, to obtain the products as a yellow solid (108.5 mg, 46.18% yield).

Example 12

The following example describes the synthesis of a porphyrin-based calcium sensor, as shown in FIG. 17. 2NH$_2$-TPPS$_3$ (5.1 mg, 5.78 μM), BAPTA-TEF (11.5 mg, 18.7 μM) and $Na_2SO_4$ (1.43 g) were mixed in 1 mL dry MeOH, and 87 μL of 0.2 M HCl in MeOH was added to the mixture, upon which the color of the reaction mixture changed from red to dark green. The reaction mixture was stirred at room temperature in the absence of light for 2.5 hours. NaBH$_3$CN (4.3 mg, 68.4 μM) was added, and the reaction mixture was stirred for 24 hours. Additional portions of BAPTA-TEF (5.5 mg 8.9 μM), $Na_2SO_4$ (1 g), and NaBH$_3$CN (3.3 mg 52.5 μM) were added, and the reaction mixture was stirred for another 24 hours. The reaction mixture was then filtered through celite and washed with MeOH. The solvents were removed, and the remaining solid residue was washed with $CH_2Cl_2$. The solid was purified by RP-18 column chromatography to obtain 1.7 mg of a disubstituted porphyrin product (14.1%) and 1.8 mg monosubstituted porphyrin product (21.0%).

What is claimed:

1. A method for determining an analyte, comprising:
providing a MRI or optical agent having the formula,

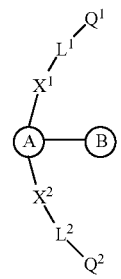

wherein:
A is a group comprising an aryl group, optionally substituted;
B is a chelator group comprising at least one aromatic heterocycle;
$X^1$ and $X^2$ can be the same or different and each is a heteroatom;
$L^1$ and $L^2$ can be the same or different and each is a group comprising an alkyl or heteroalkyl group, optionally substituted; and
$Q^1$ and $Q^2$ can be the same or different and each is a group comprising a binding moiety for an analyte;
exposing the agent to a sample suspected of containing an analyte, wherein the agent interacts with the analyte, if present, to generate an analyte-bound MRI signal or optical signal that is shifted relative to the MRI signal or optical signal absent the analyte; and
determining the shift in the MRI signal or an optical signal of the agent, or lack thereof, thereby determining the presence and/or amount of the analyte in the sample.

2. A method as in claim 1, further comprising the act of:
inserting the MRI or optical agent into a cell or portion of a cell and the analyte, if present, is within the cell.

3. A method as in claim 1, wherein the analyte is present within a subject.

4. A method as in claim 1, wherein the analyte is present within a cell.

5. A method as in claim 1, wherein the analyte is a metal ion or nitric oxide.

6. A method as in claim 1, wherein the analyte is $Zn^{2+}$, $Ca^{2+}$, $Hg^{2+}$, $Cd^{2+}$, or $Pb^{2+}$.

7. A method as in claim 1, wherein the shift in the magnetic resonance imaging signal comprises a shift in T1 relaxivity.

8. A method as in claim 1, wherein the shift in the magnetic resonance imaging signal comprises a shift in T2 relaxivity.

9. A method as in claim 1, wherein the shift in the optical signal comprises an increase or decrease in luminescence intensity, or a shift in luminescence wavelength.

10. A method as in claim 1, wherein the interaction between the agent and the analyte comprises a binding event between the binding moiety and the analyte.

11. A method as in claim 1, wherein the chelator group comprises at least one aromatic heterocycle and comprises a metal ion bound to the at least one aromatic heterocycle.

12. A method as in claim 1, wherein the agent is not linked to a carrier molecule.

13. A method as in claim 1, wherein the chelator group comprises a polycyclic group.

14. A method as in claim 1, wherein the chelator group is a porphyrin, expanded porphyrin, or polypyrrole group, optionally substituted.

15. A method as in claim 1, wherein the binding moiety is dipicolylamine (DPA) or 1,2-bis(o-aminophenoxy)ethane-N,N,N',N'-tetraacetic acid (BAPTA).

16. A method as in claim 11, wherein the chelator group comprises a metal ion bound to the at least one aromatic heterocycle.

17. A method as in claim 16, wherein the metal ion is a paramagnetic metal ion.

18. A method as in claim 1, wherein the agent has the formula,

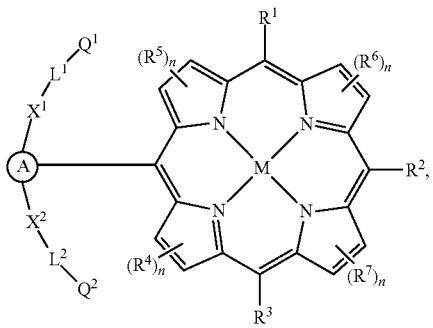

wherein:
A is a group comprising an aryl or heteroaryl group, optionally substituted;
$X^1$ and $X^2$ can be the same or different and each is a heteroatom;
$L^1$ and $L^2$ can be the same or different and each is a group comprising an alkyl or heteroalkyl group, optionally substituted; and
$Q^1$ and $Q^2$ can be the same or different and each is a group comprising a binding moiety for an analyte;
$R^{1-3}$ can be the same or different and are groups which are together selected such that the compound is water-soluble;
$R^{4-7}$ can be the same or different and each is a group comprising halide, hydroxyl, alkyl, or aryl, and each is optionally substituted;
M is absent or a metal ion such that, when M is absent, the compound comprises a free base porphyrin group and, when M is present, the compound comprises a metalloporphyrin group.

19. A method as in claim 18, wherein:
A is phenyl or pyridine;
both $X^1$ and $X^2$ are N, O, or S;
both $Q^1$ and $Q^2$ are dipicolylamine (DPA) or 1,2-bis(o-aminophenoxy)ethane-N,N,N',N'-tetraacetic acid (BAPTA);

$R^{1-3}$ are each sulfonated benzene or N-alkylated pyridinium; and
M is absent or $Mn^{3+}$, $Mn^{2+}$, $Fe^{3+}$, $Fe^{2+}$, $Zn^{2+}$, $Mg^{2+}$ or $Al^{3+}$.

20. A method as in claim 1, wherein the agent has the structure,

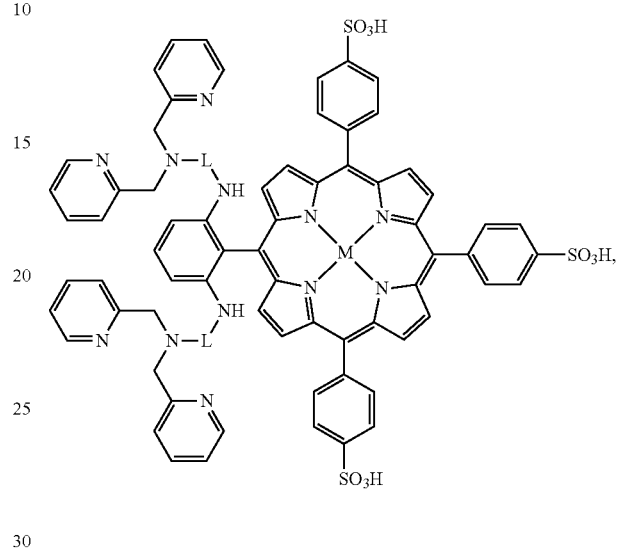

wherein L is an ethylene group and M is $Mn^{3+}$, $Mn^{2+}$, $Fe^{3+}$, or $Fe^{2+}$.

21. A method as in claim 1, wherein the agent has the structure,

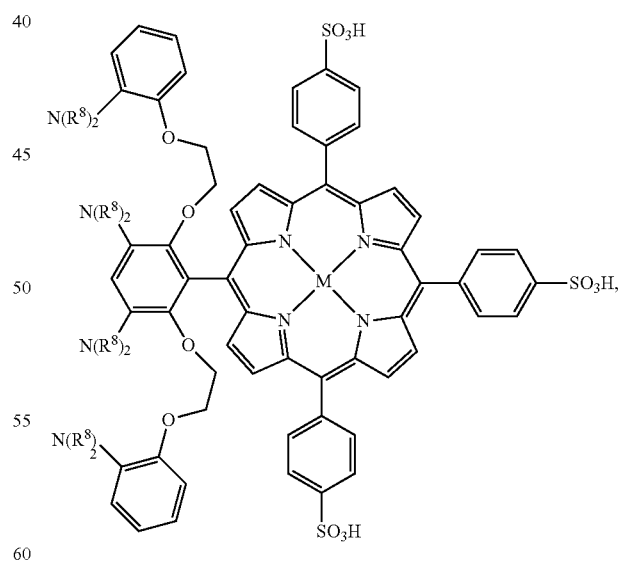

wherein M is $Zn^{2+}$, $Mg^{2+}$, $Al^{3+}$, $Mn^{3+}$, $Mn^{2+}$, $Fe^{3+}$, or $Fe^{2+}$; $R^8$ is $CH_2CO_2H$ or $CH_2CO_2R^9$; and $R^9$ is alkyl.

22. A method as in claim 1, wherein the agent has the structure,

31
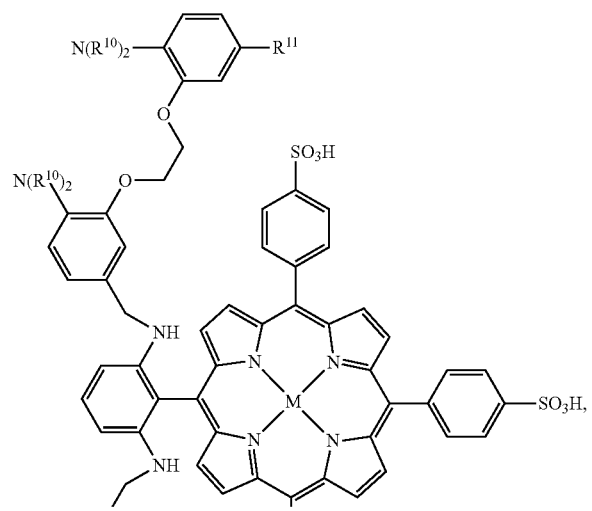
32
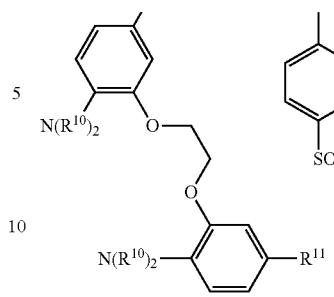
wherein M is $Zn^{2+}$, $Mg^{2+}$, $Al^{3+}$, $Mn^{3+}$, $Mn^{2+}$, $Fe^{3+}$, or $Fe^{2+}$; $R^{10}$ is $CH_2CO_2H$ or $CH_2CO_2R^{12}$; $R^{11}$ is hydrogen or alkyl; and $R^{12}$ is alkyl.
* * * * *

UNITED STATES PATENT AND TRADEMARK OFFICE
CERTIFICATE OF CORRECTION

PATENT NO. : 8,133,474 B2
APPLICATION NO. : 11/901245
DATED : March 13, 2012
INVENTOR(S) : Xiao-An Zhang et al.

It is certified that error appears in the above-identified patent and that said Letters Patent is hereby corrected as shown below:

Please delete the paragraph titled 'FEDERALLY SPONSORED RESEARCH OR DEVELOPMENT' encompassing, Column 1, lines 14-17:

"This invention was made with the support under the following government contract: 5-R01-GM065519-06 awarded by National Institutes of Health. The government has certain rights in the invention."

and replace with:

--This invention was made with government support under Grant No. R01 GM065519 awarded by the National Institutes of Health. The government has certain rights in this invention.--

Signed and Sealed this
Sixteenth Day of October, 2012

David J. Kappos
*Director of the United States Patent and Trademark Office*